(12) United States Patent
Wanderer et al.

(10) Patent No.: US 9,119,708 B2
(45) Date of Patent: Sep. 1, 2015

(54) DEVICES TO DILATE NASAL AIRWAYS FOR VARIOUS APPLICATIONS INVOLVING: ACTIVITIES USING GOGGLES WITH A HELMET OR GOGGLES ALONE; SWIMMING WITH GOGGLES, WITHOUT OR WITH A SWIM CAP; SLEEP; SLEEP WITH A CPAP MASK; AND FOR PHYSICAL ACTIVITIES

(71) Applicant: Nozewair, LLC, Bozeman, MT (US)

(72) Inventors: Alan Wanderer, Bozeman, MT (US); Ewan R. Grantham, Castle Rock, CO (US); David Yakos, Bozeman, MT (US); Seth Carlstrom, Bozeman, MT (US); Ross Walker, Belgrade, MT (US); Rebecca K. Berg, Bozeman, MT (US)

(73) Assignee: Nozewair, LLC, Bozeman, MT (US)

( * ) Notice: Subject to any disclaimer, the term of this patent is extended or adjusted under 35 U.S.C. 154(b) by 0 days.

(21) Appl. No.: 14/512,023

(22) Filed: Oct. 10, 2014

(65) Prior Publication Data

US 2015/0216710 A1      Aug. 6, 2015

Related U.S. Application Data

(60) Provisional application No. 61/978,430, filed on Apr. 11, 2014, provisional application No. 61/955,881, filed on Mar. 20, 2014, provisional application No. 61/933,935, filed on Jan. 31, 2014.

(51) Int. Cl.
*A62B 29/00* (2006.01)
*A61M 29/00* (2006.01)
(Continued)

(52) U.S. Cl.
CPC .................... *A61F 5/08* (2013.01); *A61F 9/029* (2013.01); *A61F 9/04* (2013.01); *A61M 16/0057* (2013.01); *A61M 16/0622* (2014.02); *A61M 16/0694* (2014.02)

(58) Field of Classification Search
CPC ...................................................... A62B 18/003
USPC ............. 128/200.24, 202.27, 206.11, 200.26, 128/206.25, 207.17, 848, 201.27, 206.21, 128/206.23–206.26, 206.28, 128/207.11–207.13; 351/136, 158; 606/199, 204.45, 198; 2/442, 445, 427, 2/428, 439, 440; 24/3.1, 3.3, 3.12
See application file for complete search history.

(56) References Cited

U.S. PATENT DOCUMENTS

| 1,819,738 A | 8/1931 | Daniels |
| 2,626,538 A | 1/1953 | Frum |

(Continued)

OTHER PUBLICATIONS

International Searching Authority, "International Search Report and The Written Opinion of the International Searching Authority" issued in connection to International Application No. PCT/US2015/10950, 10 pages, mailed Apr. 10, 2015.

*Primary Examiner* — Alireza Nia
*Assistant Examiner* — Tarla Patel
(74) *Attorney, Agent, or Firm* — McKee, Voorhees & Sease, PLC

(57) ABSTRACT

Medical devices are disclosed as providing nasal airway dilation in subjects in need thereof whose nasal airways are partially or completely blocked, such as for sleep; with CPAP masks; for exercise; wearing goggles alone or with helmets; and for swimming. In an aspect, the devices with a group of application provide nasal dilation to overcome obstruction caused by nasal valve dysfunction. Methods of employing the same to dilate nasal airways are further disclosed.

10 Claims, 27 Drawing Sheets

(51) Int. Cl.
  *A61F 5/08*   (2006.01)
  *A61F 9/04*   (2006.01)
  *A61M 16/06*  (2006.01)
  *A61F 9/02*   (2006.01)
  *A61M 16/00*  (2006.01)

(56) References Cited

U.S. PATENT DOCUMENTS

| | | | |
|---|---|---|---|
| 2,843,115 A * | 7/1958 | Aufricht | 606/204.45 |
| 3,502,396 A | 3/1970 | Greenberg | |
| 3,835,848 A | 9/1974 | Berner | |
| 3,879,804 A | 4/1975 | Lawrence | |
| 4,133,604 A | 1/1979 | Fuller | |
| 4,250,577 A | 2/1981 | Smith | |
| 4,657,364 A | 4/1987 | Murrell | |
| 4,774,935 A * | 10/1988 | Aronsohn | 606/204.45 |
| 4,793,702 A | 12/1988 | Ahrens et al. | |
| 5,002,381 A | 3/1991 | Murrell | |
| 5,054,903 A | 10/1991 | Jannard et al. | |
| 5,249,001 A | 9/1993 | Jannard | |
| 5,476,091 A | 12/1995 | Johnson | |
| 5,669,377 A | 9/1997 | Fenn | |
| 5,806,525 A | 9/1998 | Pope, Jr. | |
| 6,000,795 A | 12/1999 | Van Rysselberghe | |
| 6,004,342 A | 12/1999 | Filis | |
| 6,006,746 A | 12/1999 | Karell | |
| 6,053,612 A | 4/2000 | MacIntosh, Jr. et al. | |
| 6,059,408 A | 5/2000 | Bonacci | |
| 6,336,456 B1 | 1/2002 | Ruben | |
| 6,349,419 B1 | 2/2002 | Chiang | |
| 6,450,640 B1 | 9/2002 | Van Rysselberghe | |
| 6,511,176 B2 | 1/2003 | Kliot | |
| 6,860,263 B1 | 3/2005 | Scoggins | |
| 6,863,066 B2 | 3/2005 | Ogle | |
| 6,941,619 B2 | 9/2005 | Mackay et al. | |
| 7,070,273 B2 | 7/2006 | Benavides et al. | |
| 7,399,079 B2 | 7/2008 | Skuro | |
| 7,441,891 B2 | 10/2008 | Schatz | |
| 7,467,867 B1 | 12/2008 | Williams | |
| 7,556,373 B2 | 7/2009 | VanAtta et al. | |
| 7,563,271 B2 | 7/2009 | Howard | |
| 7,845,795 B2 | 12/2010 | Williams | |
| 7,862,168 B1 | 1/2011 | Yang | |
| 8,025,397 B2 | 9/2011 | Martin et al. | |
| 8,047,201 B2 | 11/2011 | Guyuron et al. | |
| 8,051,850 B2 | 11/2011 | Kwok et al. | |
| 8,240,309 B2 | 8/2012 | Doshi et al. | |
| 8,245,320 B2 * | 8/2012 | Provost et al. | 2/13 |
| D669,115 S | 10/2012 | Kalbach | |
| 8,302,607 B2 | 11/2012 | Pierce et al. | |
| 8,459,254 B1 | 6/2013 | Jassir et al. | |
| 8,491,622 B2 | 7/2013 | Brown | |
| 8,523,350 B2 | 9/2013 | Krisik et al. | |
| 8,733,926 B2 | 5/2014 | Stewart | |
| 2001/0023695 A1 | 9/2001 | Auriemma | |
| 2005/0286013 A1 | 12/2005 | Aylor | |
| 2007/0028917 A1 | 2/2007 | Veeder | |
| 2007/0113853 A1 | 5/2007 | Pavesi | |
| 2007/0255309 A1 | 11/2007 | Guyuron et al. | |
| 2009/0025715 A1 | 1/2009 | Sugden et al. | |
| 2009/0183734 A1 | 7/2009 | Kwok et al. | |
| 2011/0106140 A1 | 5/2011 | Obando | |
| 2011/0265802 A1 | 11/2011 | Ha | |
| 2012/0160240 A1 | 6/2012 | Spano | |
| 2012/0285468 A1 | 11/2012 | Birch | |
| 2013/0077043 A1 | 3/2013 | Moran | |
| 2013/0174333 A1 | 7/2013 | Schwartz | |
| 2013/0278882 A1 | 10/2013 | Stewart | |

* cited by examiner

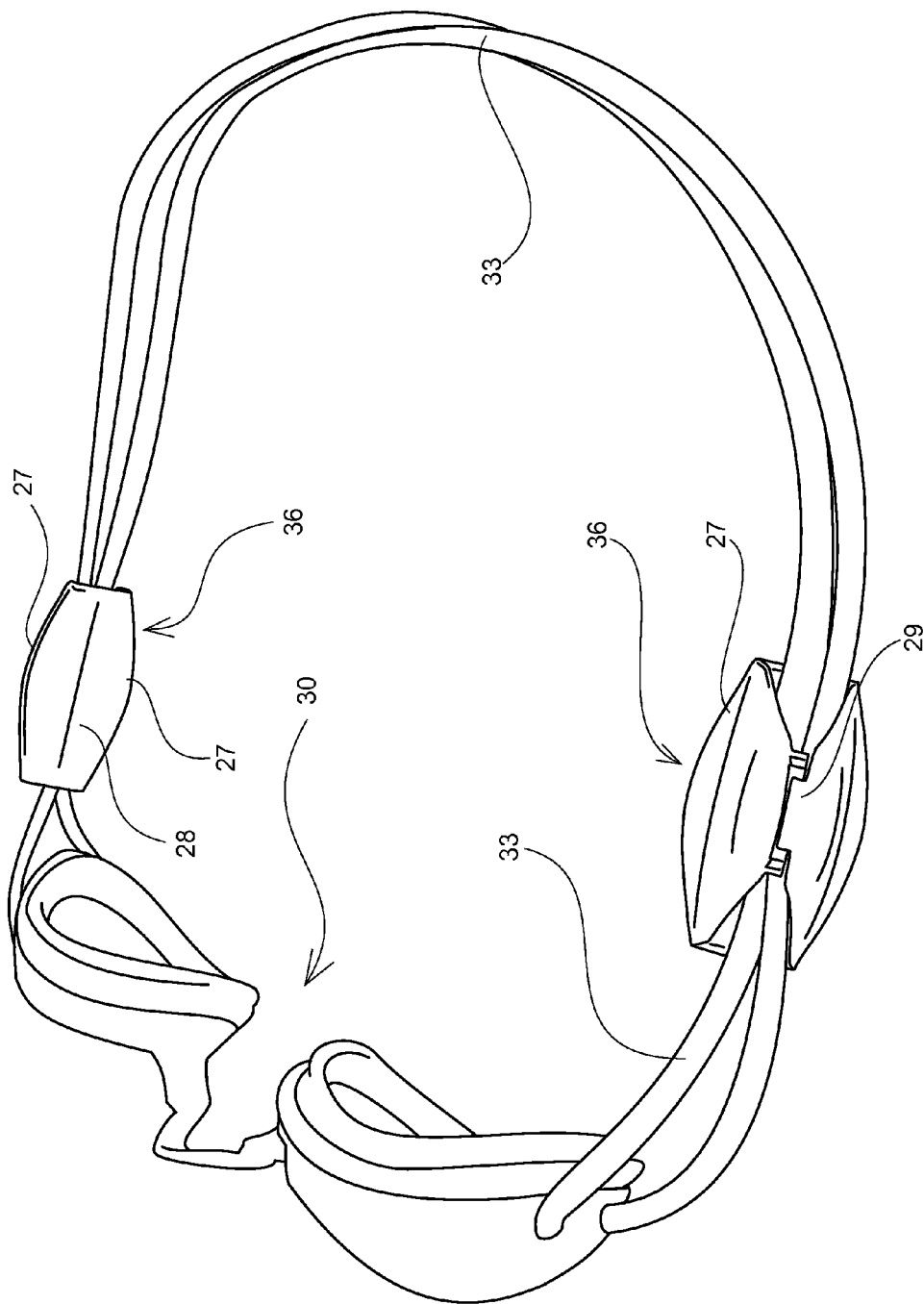

DEVICES TO DILATE NASAL AIRWAYS FOR VARIOUS APPLICATIONS INVOLVING: ACTIVITIES USING GOGGLES WITH A HELMET OR GOGGLES ALONE; SWIMMING WITH GOGGLES, WITHOUT OR WITH A SWIM CAP; SLEEP; SLEEP WITH A CPAP MASK; AND FOR PHYSICAL ACTIVITIES

CROSS-REFERENCE TO RELATED APPLICATIONS

This application claims priority under 35 U.S.C. §119 to provisional applications Ser. No. 61/978,430 filed Apr. 11, 2014, Ser. No. 61/955,881 filed Mar. 20, 2014, and Ser. No. 61/933,935 filed Jan. 31, 2014, all of which are hereby incorporated by reference in their entirety.

FIELD OF THE INVENTION

The present invention relates to the fields of medical devices for several applications such as: activities using goggles with helmets or goggles alone; swim goggles with or without swim caps; sleep alone or with a CPAP mask and physical activities. More specifically, but not exclusively, the invention relates to devices that dilate the nasal airway in subjects whose nasal airways are partially or completely blocked for any number of causes, the most common being obstruction caused by nasal valve dysfunction. The present invention provides devices and methods of employing similar elements to achieve the primary function of dilating nasal airways for these applications.

BACKGROUND OF THE INVENTION

To understand mechanisms and devices employed to improve nasal airway patency, the anatomical structure should be understood. Nasal valves are anatomically divided into external and internal nasal valves. The external nasal valve is defined for each nostril laterally by the nasal alae with the underlying caudal border of the lower lateral cartilage, the columella at the base of the septum to the tip of the nose, the nasal floor, and medially by the septum. The nasalis muscles dilate the external nasal valve during inspiration. The opening to the external valve area is sometimes referred to as the nasal vestibule formed by walls as described. The internal nasal valve compromises the area bounded by the caudal border of the upper lateral cartilage, the septum, the head of the inferior turbinate and the pyriform aperture with tissues surrounding it.

Based on simplified laminar flow equations (referred to as the Poiseuille equation), a decrease in the radius of the nasal airway causes a 4-fold decrease in flow. Hence any reduction in the opening diameter of the nasal airway, especially in the vicinity of the external and/or internal valves, will significantly reduce inspiratory and expiratory air volume and flow rates. In addition this effect will be accentuated when a subject attempts to inspire rapidly which will reduce the air pressure inside the nasal cavity as compared to atmospheric pressure, and thereby cause more collapse of the affected nasal airway, i.e. Bernoulli effect. This effect becomes noticeable with vigorous exercise that is associated with rapid respiratory rates.

There are many causes of nasal obstruction. A common cause is idiopathic in which there is a reduction of cartilage and/or elastic tissue support needed to maintain patency of the valves both external and internal. In particular loss of support often involves the external valves and/or prolapse of the nasal tip of the nose. As aging occurs this effect can become more noticeable. Other causes of nasal obstruction include septal deviation; turbinate hypertrophy from allergy and/or rebound swelling from overuse of vasoconstrictor nasal sprays; trauma-induced; iatrogenic post-rhinoplasty; foreign bodies; neoplasm and polyps and from other less common medical conditions. A health care provider can evaluate the cause of nasal obstruction visually with rhinoscopes; CT scan; MRI; measurement of air flow; and by a simple test of valve patency, commonly referred to as the Cottle test. In this test the subject is instructed to gently obstruct one nostril at a time with a finger to determine subjective reduction of inspiratory nasal air flow involving the contralateral nostril. Then the subject is instructed to place one or two fingers on the lower side of the contralateral nostril at the nasal-facial angle, and stretch the skin toward the ipsilateral ear. The procedure is repeated for the other nostril. If the nasal valve (external and/or internal) is partially or completely obstructing air flow, stretching the skin laterally will pull on the underlying tissues attached to the nasal valves and/or vestibules and open them to improve air flow/volume into that tested side of the nasal cavity. The Cottle test is considered a subjective diagnostic test for the presence of nasal valve obstruction. It is sometimes used by plastic or ENT surgeons to determine if a subject might be a candidate for a rhinoplastic procedure to improve nasal obstruction and/or as a post-operative test to validate improvement in nasal airway obstruction. Although not specifically described by the Cottle effect, a similar stretching of skin posterior of the lateral canthi in a lateral and somewhat superior vector can also effect nasal valve/vestibule patency. This effect is discussed in the description of the invention herein as it is applied to swim goggles.

There are many marketed devices available to improve nasal airway patency in subjects with obstruction from external/internal valves. The purpose of these devices is to ease airway flow during sleep or exercise and to reduce snoring. In some situations, nasal obstruction may force a subject to breathe through the mouth, which will exacerbate snoring due to oral-pharyngeal tissue vibrations. In some subjects with sleep apnea, severely impaired nasal obstruction with or without associated mouth breathing, can exacerbate severity of sleep apnea and also make it more difficult to correct sleep apnea with nasal or full face continuous positive airway pressure (CPAP) masks.

Marketed nasal dilator devices fall into three categories. The first are external devices associated with adhesive tape applied to the nose (e.g. U.S. Pat. No. 5,476,091; U.S. Pat. No. 5,806,525), and/or to the nasal alae (e.g. U.S. Publication No. 2007/0255309; U.S. Pat. No. 8,047,201), and/or to the tip of the nose (e.g. U.S. Pat. No. 5,669,377; U.S. Publication No. 2011/0106140). These nasal devices with adhesives contain resilient spring or biasing mean(s), that when applied to the various locations of the nose, cause the attached skin and underlying tissue(s) to open the nasal valves and thereby improve nasal air flow in the subject. These tapes come in a variety of shapes, can be placed on various locations of the nose and/or face, contain a variety of spring mechanisms and use different kinds of adhesives. A limitation of such tapes are they are designed to be used one time and disposed and cannot be relocated easily for comfort or to adjust to improve nasal valve opening because adhesive tape loses its ability to adhere if removed and reattached. Hence they are expensive, environmentally objectionable, cannot be relocated easily, are not reusable, and on a personal level subjects often stop using them because they peel off under oily or sweaty skin, thereby defeating their purpose to improve nasal air flow during sleep or with physical activities. They can cause discomfort when peeled off, and individuals who use facial lotions, cannot achieve good adherence to their nose and/or face with these adhesives. Additionally subjects using these tapes may notice transient swelling of the nasal alae and vestibules, which is unsightly and may be caused by venous pooling and reduced venous outflow from the nasal tissues while wearing the tapes.

A newly marketed device (U.S. Pat. No. 8,240,309; U.S. Pat. No. 8,302,607) called Theravent® uses a tape to occlude both nostrils. The tape includes a micro-valve technology that inhibits expiration more than inspiration to create expiratory positive airway pressure within the nasal-pulmonary respiratory tract. The increase in expiratory resistance can retain air volume that expands the diameters of the nasal-respiratory tract and thereby improve nasal airflow during inspiration. It is costly as a disposable, can cause whistling through one way valves during respiration, may not work if the air pressure seal is broken by mouth breathing and users express discomfort noticing that before falling asleep they cannot breathe normally because of increased expiratory resistance. They also cannot be relocated and reattached easily as adhesive tape loses its adherent ability once removed and then reattached. U.S. Pat. No. 6,006,746 shows adhesive pads with a resilient nasal dilator member to attach to eyeglasses. The adhesive attaching means interfere in adjustment of the eyeglass for optimizing visual acuity once the adhesive attachment of the nasal dilator is in place. Also the adhesive nasal dilator can only be used one time.

U.S. Pat. No. 8,051,850 shows a nasal dilator device with attaching means for contact pads that use adhesives or friction pressure to keep the contact pads from pulling off a user's face. As will be best understood with the description of the benefits of the present invention, the disadvantages of structure FIG. 5 in U.S. Pat. No. 8,051,850 for a nasal dilator are: (1) it employs a completely circumferential elastic head band that can be displaced by user head movement and thus makes it difficult to maintain forces for nasal dilation to either or both sides of user's nose; (2) it does not include a mound that provides added moments of forces to enhance opening nasal passages (3) it does not include a holding means for mound(s) to maintain mound positioning; and (4) it does not include means to adjust and/or relocate and/or reuse contact pads to same or different location(s) in relation to user's nose and/or face and/or head as needed to improve nasal patency and/or patient comfort. Instead it uses contact pads that are held on the user's face by adhesives or friction that minimize easy repositioning if needed. The adhesives lose their attaching means once removed and repositioned, and both adhesives and friction means cause difficulty maintaining positioning when an active exerciser sweats or experiences facial distortions during exercise which will lessen adherence to a user's face. In an iteration of U.S. Pat. No. 8,051,850, FIGS. 5 and 6, show adhesive contact pads for a nasal dilator with a strap over the resilient nasal dilating spring that will vector posteriorly onto the user's nose and reduce the objective of achieving maximum nasal valve and/or vestibule patency. In U.S. Pat. No. 8,051,850, FIG. 8 shows an embodiment of a nasal dilator for a CPAP mask with laterally pulling forces using adhesive or friction contact pads held by the posterior vectored force of CPAP mask head retainer straps. This embodiment has limitations in repositioning, adjustment or reuse of the contact points and doesn't include a mound(s) for enhancing moment of force for nasal dilation nor a means to hold said mound(s). FIG. 9 in same patent for CPAP masks, applies a nasal dilator with an adhesive with previously described inherent disadvantage, all integrated into a CPAP mask and is also void of a mound element to enhance nasal dilation. As a result, there remains numerous commercial disadvantages with these various devices employing tape, friction holding means or other adhesive elements.

The second category of nasal dilators (e.g. U.S. Pat. No. 6,863,066; U.S. Pat. No. 6,004,342; U.S. Pat. No. 7,563,271) are spring-like nasal dilators that are inserted inside the nostrils to expand the volume of air space inside the vestibules. These devices are made of metal or plastic, and have a resilient spring mechanism that expand the vestibules in many directions, particularly anteriorly and laterally. Subjects are instructed to leave them in situ inside the nasal cavities during sleep and/or exercise. The problems and limitations with these devices include: (1) they behave as a foreign body inside the nose and may cause discomfort, itching, and in some subjects, reflex sneezing. There are also case reports in the medical literature involving these devices being displaced unknowingly inside the nose of users and creating foreign body-induced inflammation; (2) they can cause pressure induced erosions and epistaxis; (3) they have the potential to irritate and enhance neuro-reflex induction of nasal mucosal swelling and rhinorrhea and thereby increase nasal obstruction; (4) they should be cleaned optimally each day before reinserting them inside the subject's nose to prevent bacterial contamination and infection inside the nostrils; (5) wearing them especially when turning over in bed during sleep or during exercise can cause them to fall out of the nose and (6) additionally subjects using these devices may notice post-use swelling of the nasal alae, which although transient, is unsightly and may be caused by venous pooling from reduced nasal venous outflow while wearing the devices.

A third category uses a head band or mask to enhance nasal valve opening and combines adhesive or non-adhesive attaching means for nasal dilator function. For example, U.S. Pat. No. 8,459,254 describes a device using an adhesive to attach an elastic band to each side of the nose. The elastic band wraps over the ears circumferentially around the back of the head to permit tightening and attaching the device to the user's face and head. By stretching the head retainer strap laterally on the user's face, the attachment sites of the skin pull open the nasal valves per the Cottle effect. It employs a completely circumferential elastic head band that can be displaced by user head movement and thus makes it difficult to maintain forces for nasal dilation to either or both sides of user's nose. The adhesive could be pulled off the skin if the stretch pressure exceeds the force of adhesive attachment to the skin. Moreover, some users cannot tolerate adhesives because they cause contact skin irritation and users who apply facial creams or lotions may have difficulty keeping adhesive tape in place. There is also specific mention that the invention avoids coverage over a subject's nose. Once the adhesive is applied, then adjusting the mask for comfort or to improve opening the valves becomes difficult, as most adhesives curl up or lose their adherence ability when they are pulled off and reapplied. In essence, this category of devices does not have an easy reversible adjustable, repositionable or reusable means to obtain an optimal comfortable lateral pull to open the nasal valves nor can it be reused without changing the adhesives. Moreover because it employs a circumferential elastic band and not a rigid or semi-rigid housing, the forces distributed to either or both sides of the user's nose for nasal dilation can be dissipated by displacement of the head band with user head movement. This nasal valve opening device can attach to eye glasses directly to the device using adhesive means to attach to a user's face that doesn't permit adjustment, and as such, it is apparent the device must remain permanently attached to the skin of the user which would otherwise preclude visual optimization for the user. Other similar devices (e.g. U.S. Publication No. 2007/0028917; U.S. Publication No. 2001/0023695; U.S. Publication No. 2009/0025715; and U.S. Pat. No. 6,860,263) also utilize adhesive tape means for attachment on each side of a user's face to open nasal valves.

U.S. Pat. No. 6,336,456 and U.S. Publication No. 2012/0285468 describe a surgical and ventilation mask respectively, both worn about the nose and face and tied about ears and head. Both include a nasal dilator mechanism comprised of adhesives strategically located inside the masks. U.S. Pat. No. 6,336,456 describes the adhesives both on the inside of the mask and on opposing sides of the user's nose. When the adhesive tapes on the user's skin and inside the mask attach to each other, the mask has an inherent resilient spring which forces the mask to return to its original configuration, and thereby cause nasal valves to open when the skin overlying the user's nose moves away, anteriorly and laterally. The adhesive resilient spring may improve external nasal valve patency but it does not provide for an adequate lateral vector pull to open the internal and external nasal valves. The described nasal dilator of U.S. Pat. No. 6,336,456 is in essence a hybrid of the external type of nasal dilator previously described, but with a mask containing the resilient member rather than having the resilient member located within the adhesive parts. Therefore, it has the same limitations using adhesive tape as it cannot be reused or relocated easily and/or adjusted for comfort to improve nasal airway function. In addition, the mask disclosed in U.S. Pat. No. 6,336,456 covers most of the face, including mouth and nose, and likely comes in contact with the user's nose, all part of it functioning as a surgical mask.

U.S. Publication No. 2012/0285468 shows a ventilation mask containing an adhesive material to open the nasal valves. U.S. Publication No. 2012/0160240 describes a mask for a subject to wear to occlude light that may interfere with sleep and improve nasal breathing by decreasing nasal valve obstruction. These devices do not include an adhesive and instead include an elastic tightening means that encircles the user's head. The dilator function occurs by applying pressure directly onto the nose to cause the nostrils to expand. Its disadvantages are: (1) it applies inward posterior forces onto the nose and doesn't take advantage of the Cottle effect to maximize nasal vestibular and nasal valve patency; (2) it can reduce nasal vestibule volume by applying direct posterior vector pressure on the nose; and (3) the overall pressure applied to the nose creates user discomfort especially during sleep.

U.S. Publication No. 2011/0265802 shows a device worn to prevent mouth opening during sleep to minimize snoring. The forces apply a tightening vector above the upper lip and below the lower lip and under the chin to maintain closure of the mouth. These forces oppose the lateralizing forces needed to open the nasal valves and the device does not include an element to cross over and not contact the nose to optimize lateral forces.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

These aforementioned exemplary devices represent the commercially available options other than rhinoplasty; implant insertion both permanent and temporary to support and maintain internal valve patency; injection of a biomaterial to support the internal valve; nasal curettage using mechanical and/or a variety of electro-magnetic energy to improve nasal airway patency involving the nasal valves. Rhinoplasty may actually cause nasal airway obstruction when cartilage and other supporting structures are altered or resected as part of the procedure. It is estimated that ten percent of post-rhinoplasty subjects experience nasal obstruction.

Advantages of nasal breathing are well known as nasal breathing filters inspired air, humidifies dry air and warms cold air. Mouth breathing is undesirable during sleep and exercise, as it causes uncomfortable mouth dryness, dehydration and increases the likelihood of dental caries. There are also training devices, such as the Frolov breathing device, and educational web sites (e.g. www.normalbreathing.com) devoted to teaching how to improve nasal breathing over mouth breathing. Several claims are made regarding the advantage of nasal breathing versus mouth breathing. One claim states that nasal breathing retains more carbon dioxide in the upper respiratory tract which increases alveolar $CO_2$ concentration on inspiration, thereby improving alveolar capillary vasodilation from retained $CO_2$ and ultimately enhancing oxygen exchange into the circulation. Learning to breathe through one's nose requires constant conscious training which is not applicable to sleep and hence would not likely be effective for most individuals.

Hence there is a need in the art for devices and methods of use thereof that maintains and improve patency of the nasal valves and/or nasal vestibules without all the inherent risks and objections associated with existing nasal dilators. The present invention for various applications overcome these risks and objections as disclosed herein. The Detailed Description of the applications of the invention, utilize the Cottle effect by applying external forces around the user's nose, and/or face and/or head that cause underlying intricate anatomical attachments to the nose to open the nasal passages.

It is therefore a primary object, feature and/or advantage of the present invention to overcome deficiencies in the art of nasal dilation.

It is another objective, feature and/or advantage of the present invention to provide a nasal dilator device and method of use that aids in opening nasal valves, and/or nasal vestibules, can be adjusted, relocated, reused and retained on the user without easily falling off during sleep or during physical activity and exercise.

It is another objective, feature and/or advantage of the present invention to provide a nasal dilator device and method of use that opens nasal valves and/or nasal vestibules by including a housing or shell with a bridge located at any single or combination of locations such as over, above or below the nose, that apply forces on each side of the nose to improve nasal patency.

It is another objective, feature and/or advantage of the present invention to provide a nasal dilator device and method of use that can be worn for many applications such as for: sleep alone; sleep with a CPAP mask; snow related sports, motor biking related and contact or non-contact sports; for tactical military users; and swimming with goggles or with swim caps.

It is another objective, feature and/or advantage of the present invention to provide a nasal dilator device and method of use that provides comfort for the user both during sleep and/or during physical activities.

It is another objective, feature and/or advantage of the present invention to provide a nasal dilator device and method of use that can be customizable by altering dimensions, shapes, and material composition, so that users with different facial and head shapes and/or nasal dimensions can wear the device and still accomplish the same function to open the nasal valves and/or vestibules.

It is another objective, feature and/or advantage of the present invention to provide a nasal dilator device and method of use to improve nasal passage patency and reduce mouth breathing.

Other objects, advantages and features of the present invention will become apparent from the following specification taken in conjunction with the accompanying drawings.

SUMMARY OF THE INVENTION

In an aspect of the present invention, the nasal dilator devices for various applications are accessories or integrated with existing manufactured products for applications worn on user's heads and/or faces. The invention discloses novel devices capable of opening the external and/or internal nasal valves and/or nasal vestibules and methods of use thereof. The invention has been devised for a variety of applications for improving nasal airway patency for: sleep alone; sleep with a CPAP mask; using goggles with a helmet or goggles alone for snow related sports, motor biking, contact and non-contact sports and for military users; and for swim goggles alone or with swim caps.

According to the invention, the nasal dilating devices for each of the various applications of use have common Essential Elements including (1) a rigid or semi-rigid housing with a bridge providing means for maintaining adjusted forces for nasal dilation involving either or both sides of user's nose; (2) a bridge(s), as part of the housing, located at any single or combination of locations over, below or above the user's nose to distribute nasal dilating forces to either or both sides of a user's nose and/or face; (3) mound(s) to enhance moments of forces for nasal dilation; (4) a holding means for mound(s) to maintain their positioning; (5) means for attachment of tightening means to housing; (6) capability of changing and varying tightening means onto mounds to open nasal passages i.e. nasal valves and/or nasal vestibules; (7) ability to adjust and/or relocate a mound to same or different location(s) in relation to user's nose and/or face and/or head as needed to improve nasal patency and/or patient comfort; and (8) reusability.

The nasal dilating devices for applications according to the invention are listed in the order in which they are described herein. They apply to: (1) goggles (also referred to as eyewear in the public domain) with or without a helmet for activities such as skiing, snowboarding, snowmobiling, dirt biking, contact or non-contact sports and military tactical use, etc.; (2) swim goggles alone or with swim caps; (3) hybrid mask for sleep and/or for contact or non-contact sports; and (4) CPAP masks. The Essential Elements apply to all the above applications and their embodiments thereof. As one skilled in the art will ascertain based on the disclosure of the invention, some of the applications may include additional components designed to overlap user's eyes. The nasal dilating device with Essential Elements described herein for applications with an eye covering component does not detract from the capability to achieve nasal passage dilation for these applications.

In an aspect, the device includes a housing or shell made of a rigid and/or semi-rigid material comprising a bridge located at any single or combination of locations, i.e. above, over and below the user's nose; mounds on either or both sides of the nose and/or face and/or head which will cause the nasal valves and/or nasal vestibules to open when a variable tightening means attached to the housing apply forces onto the mounds laterally, and/or superiorly and/or inferiorly or any vectored direction to accomplish this function. In a further aspect, the mounds may be permanently or reversibly attached, adjustable, re-locatable and reusable for optimal function and are located in regions on or close to the nasal-facial interfaces and/or over or around the maxillary regions, zygomatic arch region, and sides of the head.

Without being limited to a particular mechanism of action according to the applications and embodiments of the invention, the mounds provide moments of forces so when the device is activated by tightening means, the skin and anatomical structures attached to the nasal valves and/or vestibules are stretched and pulled to open the external and internal nasal valves and/or nasal vestibules bilaterally or unilaterally, and can also move the nasal tip superiorly and slightly posteriorly away from the upper lip. Beneficially, according to applications and embodiments of the invention, these maneuver(s) assist in improving and maintaining nasal patency and thereby enhance nasal airflow. As described according to various applications and embodiments of the invention, the devices can be adjusted, relocated, reused, removed and reattached for comfort and/or to improve nasal patency during sleep with and without CPAP masks, wearing goggles alone or in combination with a helmet, wearing swim goggles alone or with swim caps and for contact or non-contact sports.

Still another aspect of the present invention is a device for sleep apnea patients who use CPAP but whose nasal airways are compromised secondary to nasal valve dysfunction. The various applications and embodiments of the invention provide suitable devices to be worn in conjunction with a full face and/or nasal CPAP mask, thereby improving nasal passage opening, also reduce air leaks and/or cheek puffing out due to high pressures when using CPAP masks.

In an additional aspect, the nasal dilating device described herein can be an accessory or integrated into various components of aforementioned applications.

While multiple applications and embodiments are disclosed, still other embodiments of the present invention will become apparent to those skilled in the art from the following detailed description, which shows and describes illustrative embodiments for applications of the invention. Accordingly, the drawings and detailed description are to be regarded as illustrative in nature and not restrictive.

Figure 1:
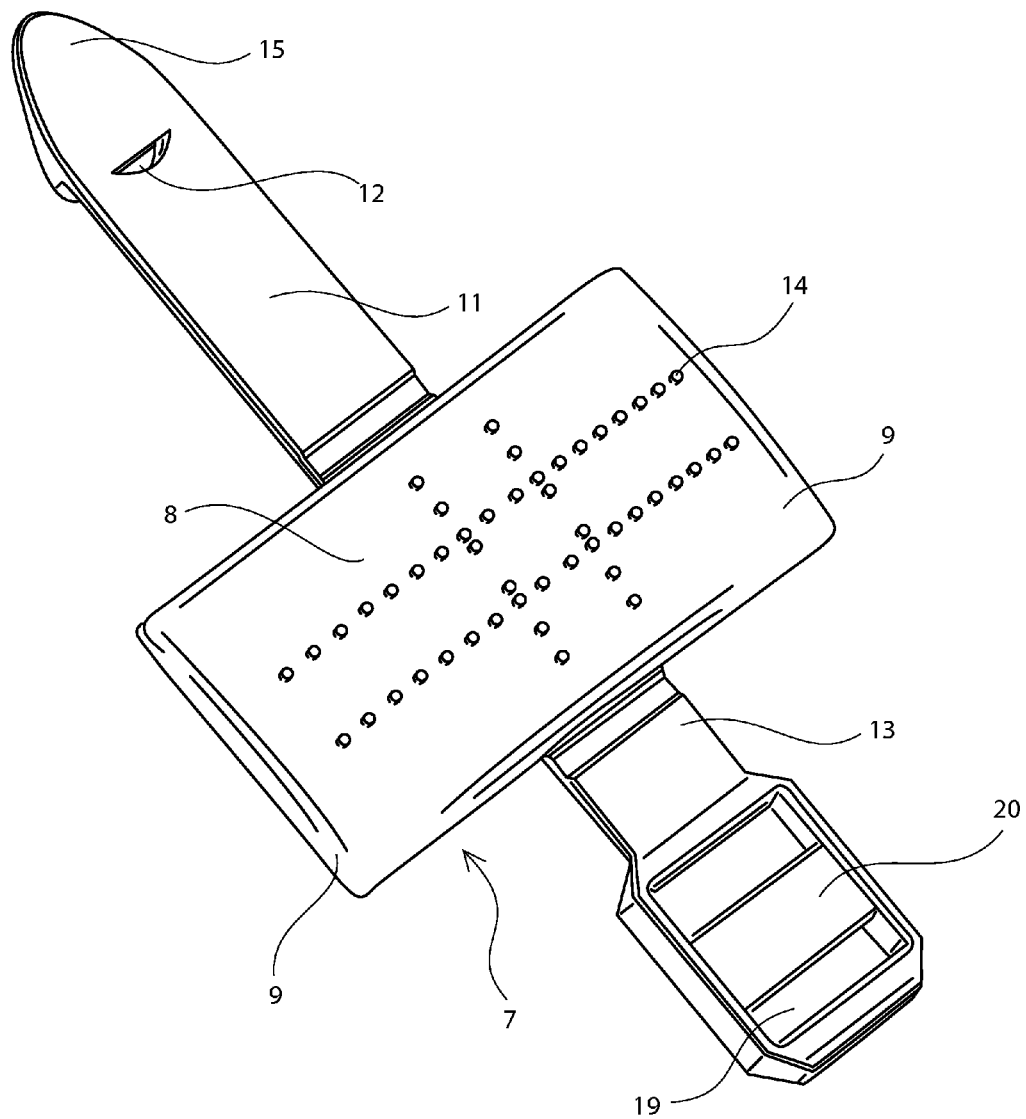
FIG. 1 shows a top view of a convex dome shaped mound according to an embodiment of a nasal dilator device for applications with goggles with a helmet or for goggles alone.

Various applications and their embodiments of the present invention will be described in detail with reference to the drawings, wherein like reference numerals may be used to represent like parts throughout the several views. Reference to various embodiments does not limit the scope of the invention. Figures represented herein are not limitations to the various embodiments according to the applications of the invention and are presented for exemplary illustration of the invention.

DETAILED DESCRIPTION OF THE INVENTION

Nasal Dilator Devices for Various Applications

The present invention relates to nasal devices that dilate the nasal airway in subjects whose nasal airways are partially or completely blocked. As mentioned previously, the various applications and embodiments of the devices according to the invention can be worn to improve nasal breathing. Applications for the devices according to the invention optimize nasal breathing for aerobic activity involving skiers, snow boarders, snowmobilers, motor/dirt bikers, runners, bikers, contact sports, military users, swimmers, and for sleep with and without a CPAP mask. The devices improve nasal breathing according to the applications and embodiments of the invention. Nasal breathing has many advantages such as improving filtering of inspired air, warming cold air and humidifying dry air. In particular warming cold air during snow sports, reduces cold induced mucus formation with nasal drainage, swelling and congestion of the lining of the respiratory tract, and in some asthma prone individuals, it reduces bronchospasm symptoms, such as wheezing, cough and shortness of breath. Additionally nasal breathing reduces mouth breathing which can cause dehydration, dryness in the mouth and increased dental caries.

The various embodiments and applications of this invention are not limited to particular devices and/or methods of nasal dilation, which can vary and are understood by skilled artisans based on the disclosure provided herein. It is also understood that all terminology used herein is for the purpose of describing particular embodiments only, and is not intended to be limiting in any manner or scope. For example, as used in this specification and the appended claims, the singular forms "a," "an" and "the" can include plural references unless the context clearly indicates otherwise. Further, all units, prefixes, and symbols may be denoted in their SI accepted form. Numeric ranges recited within the specification are inclusive of the numbers defining the range and include each integer within the defined range.

Unless defined otherwise, all technical and scientific terms used herein have the same meaning as commonly understood by one of ordinary skill in the art to which the embodiments of the applied invention pertain. Many methods and materials similar, modified, or equivalent to those described herein can be used in the disclosed applications of the devices and/or practice of the embodiments of the present invention without undue experimentation; the preferred materials and methods are described herein. In describing and claiming the embodiments of the present invention applications, the headings provided are not limitations on the embodiments of the invention and the following terminology will be used in accordance with the definitions set out below.

The methods, systems, and devices/apparatuses of the present invention may comprise, consist essentially of, or consist of the components of the present invention as well as other components or functional equivalents described herein. As used herein, "consisting essentially of" means that the methods, systems, and devices/apparatuses may include additional steps and/or components, but only if the additional steps and/or components do not materially alter the basic and novel characteristics of the claimed methods, systems, and devices/apparatuses.

It should also be noted that, as used in this specification and the appended claims, the term "configured" describes a system, apparatus, or other structure that is constructed or configured to perform a particular task or adopt a particular configuration. The term "configured" can be used interchangeably with other similar phrases such as arranged and configured, constructed and arranged, adapted and configured, adapted, constructed, manufactured and arranged, and the like. It is also noteworthy that the terms goggles and eyewear maybe used interchangeably in these specifications.

Applications of Nasal Dilator Devices
Nasal Dilating Device(s) Applications for Goggles Alone or for a Combination of Goggles with a Helmet.

Figure 5:
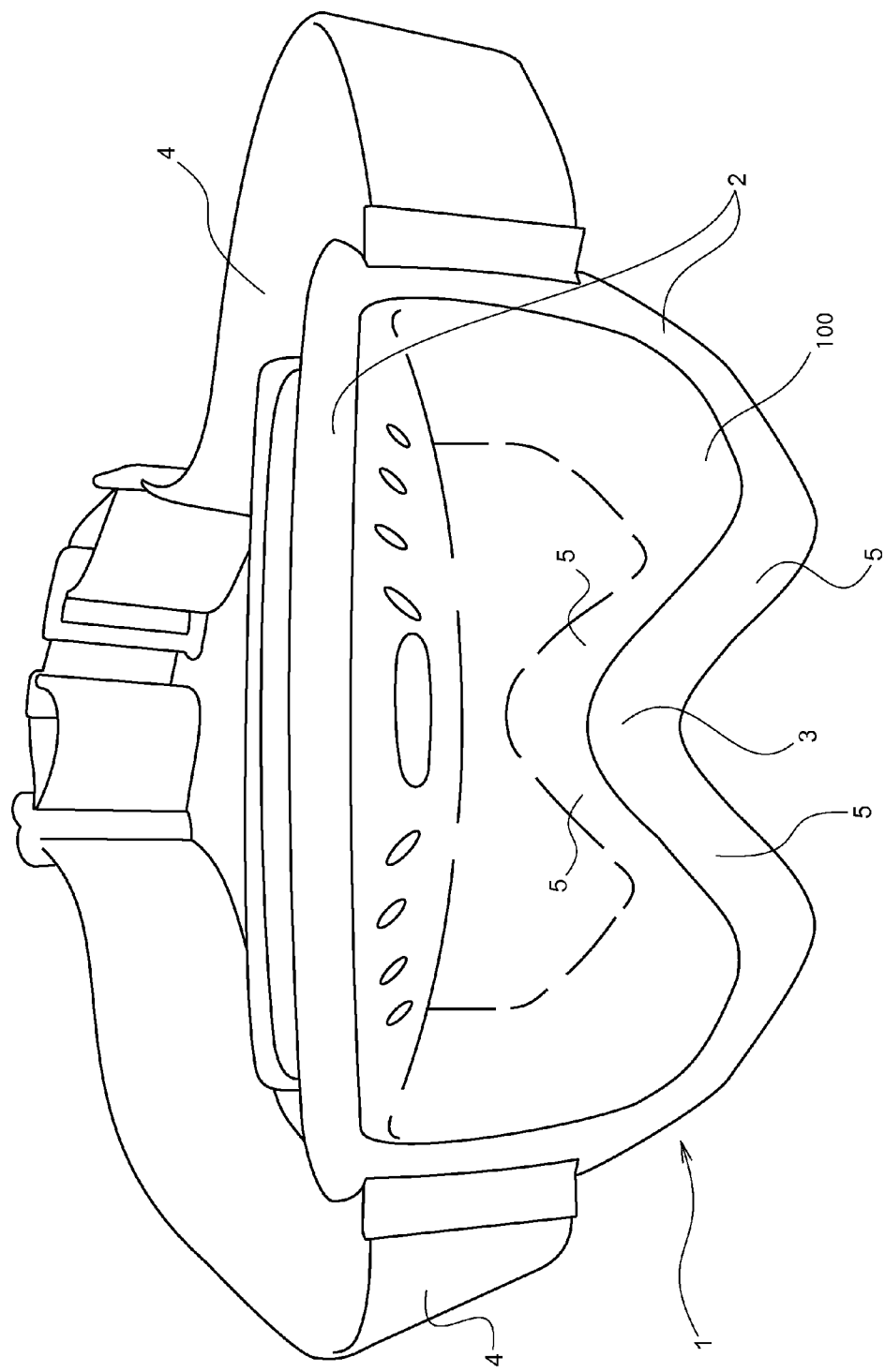
FIG. 5 shows an exemplary type of goggles such as for skiers or dirt bikers suitable for use with the nasal dilator devices according to the invention.

FIG. 5 shows goggles 1, (also referred to as a goggle-mask), with a rigid or semi-rigid housing 2 with a bridge 3 that arches above and/or over the user's nose and head retainer strap 4 attached to the housing 2 to stretch and tighten the goggles 1 around the user's head. As will be recognized, the rigid or semi-rigid housing 2 with a bridge 3 provides means for maintaining adjusted forces for nasal dilation to either or both sides of user's nose. The goggles 1 surround or overlap the eyes of the user with a clear eye protector 100 and includes a cushion liner 5 to interface between the user's face and the housing 2 portion of the goggles 1. When goggles 1 are worn, they may compress the nose and reduce nasal passage patency and even worsen pre-existing tendencies for nasal obstruction, commonly referred to as nose squeeze. In cold weather, nasal patency is worsened because of solidification of water and mucus at the entrance to the nares. Goggles have no inherent means to enhance nasal dilation to improve warming of air during nasal inspiration and to minimize water loss that occurs by breathing through the mouth during vigorous exercise as with winter sports. Moreover, wearing goggles on top of a commercially available adhesive nasal dilator strip (e.g. Breathe-Rite®) defeats the function of a nasal dilator, as the inward posterior vectored pressure of the goggles on top of the nasal dilator strip can prevent functioning of the resilient nasal dilator expander. According to an embodiment of the present application of the invention, a nasal dilator can be added for example to a skier's or dirt biker's goggles with a helmet to achieve the nasal dilator function of this invention.

Figure 6:
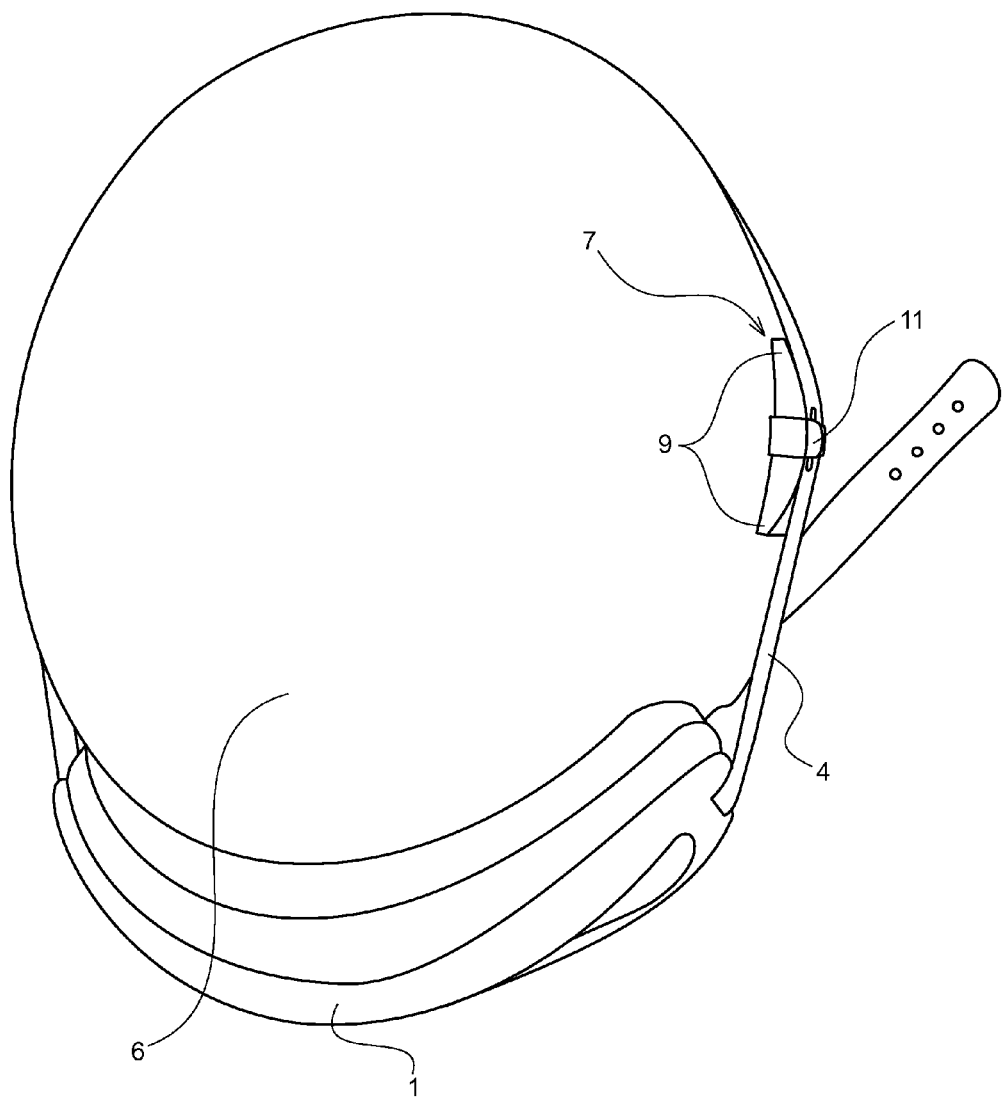
FIG. 6 shows top view of a mound embodied in FIGS. 1 and 2 with fill in sloping anterior and posterior sides located between the head retainer strap of goggles and the side of a helmet, according to an embodiment of a nasal dilator device for this application.
Figure 7:
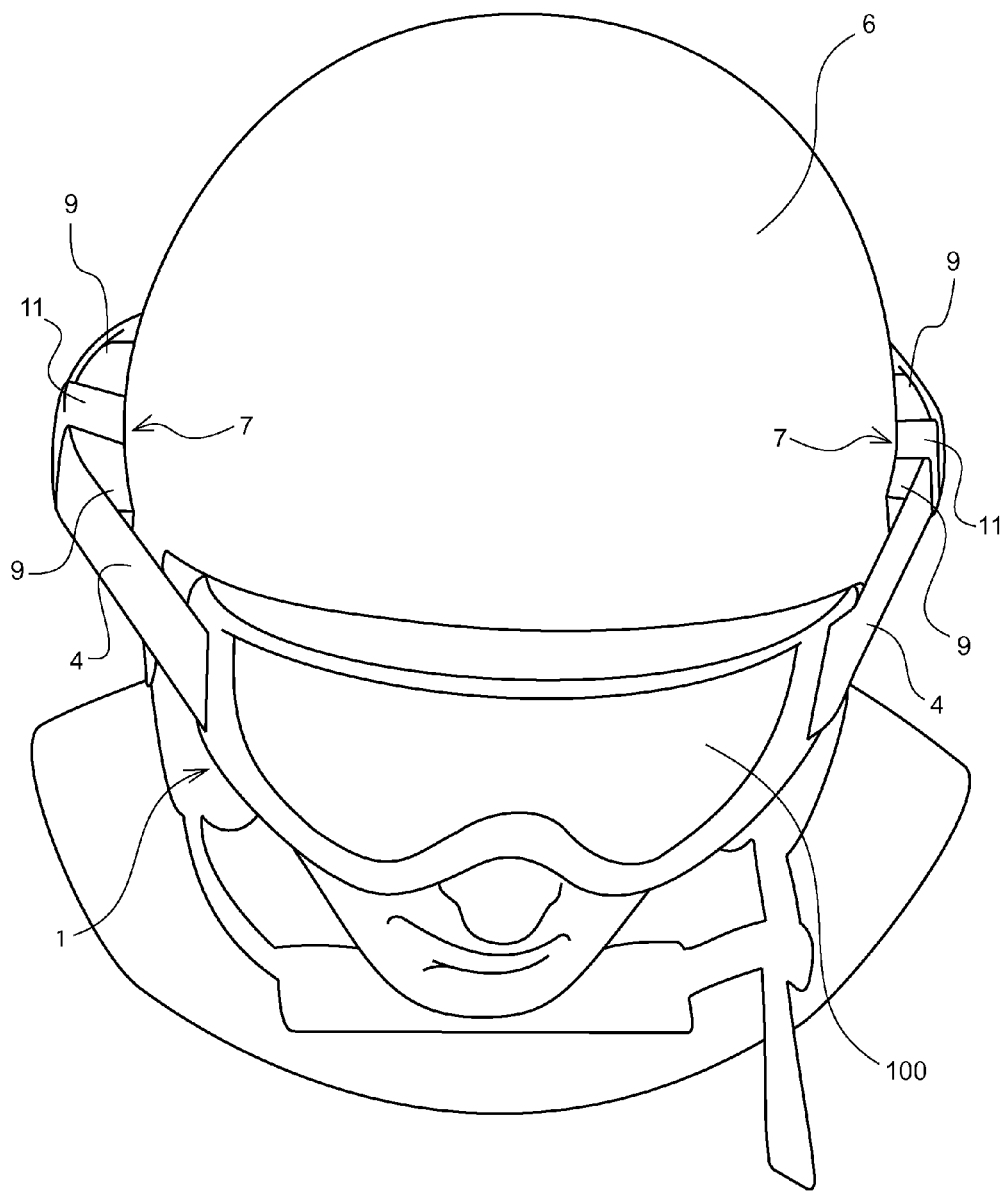
FIG. 7A shows a top and front view of a user wearing a combination of goggles and helmet with mounds shown in FIG. 1 located between the goggle strap and helmet, according to an embodiment of a nasal dilator device for this application.
FIG. 7B shows a side perspective of a helmet with a break away view of a rail and lip with overhang to accommodate attachment of a mound without straps (straps 11, 13 are depicted in FIG. 1) according to an embodiment of a nasal dilator device for this application.
FIG. 7C shows a top view of protective goggles/eyewear for contact sports, according to an embodiment of a nasal dilator device for this application.
Figure 7:
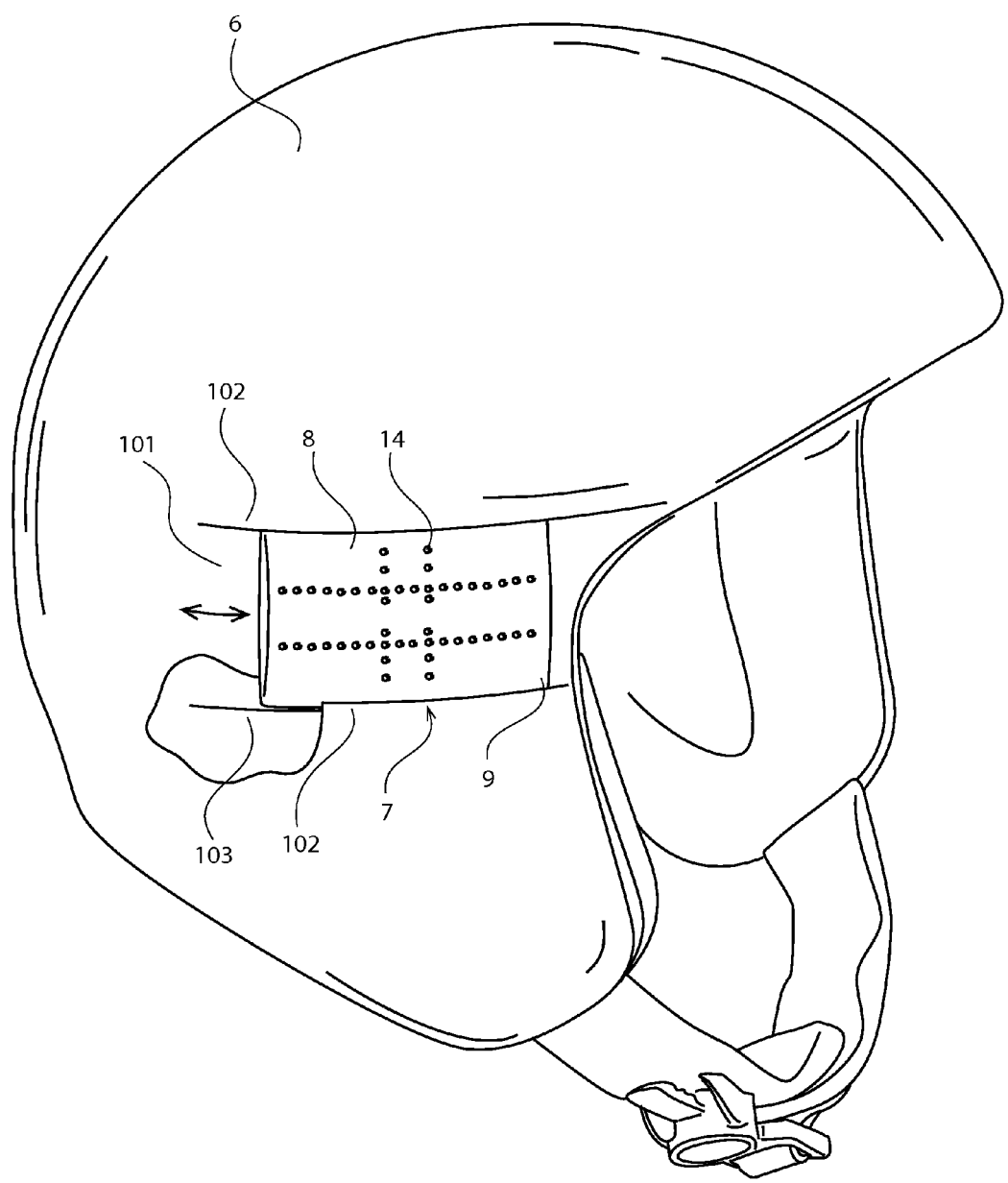
Figure 7:

The device for goggles 1 and for the combination of goggles attached to a helmet 6, shown in FIGS. 6 and 7 A, utilize the addition of mounds 7, FIG. 1. The mounds 7 are made of a semi-rigid or rigid plastic as described in more detail. The elastic head retainer strap 4 is located over and on the top or apex 8 of the mound 7 so that the mound 7 is located between the head retainer strap 4 and the side of the helmet 6. A user can add a mound 7 to a head retainer strap without using a helmet, but a preferred softer material constructed mound is advised for safety reasons if there is no helmet protecting the user's head. Newer helmets with soft ears still provide a hard surface for placing the mound 7 between the head retainer strap 4 and the lateral side of the helmet 6. In either usage the mound 7 is held in place by the inward vectored pressure of the head retainer strap 4 onto the mound 7 and helmet 6 or to the sides of the user's head. The cushion liner 5 of the goggles 1, which is in contact with the user's skin around the nose and other regions of the user's face, will stretch and apply forces to the contacted underlying skin. The facial skin has complex underlying anatomical structures (connective tissue fascia etc.) interconnected to the nasal valves and/or nasal vestibules, and consequently the resultant vectored forces, (i.e. such as laterally, inferiorly, superiorly posteriorly), will pull and cause the nasal valves and/or nasal vestibules to expand and thereby improve nasal passage patency. The rigid or semi-rigid housing 2 with a bridge 3 provide means for maintaining adjusted forces for nasal dilation for either or both sides of user's nose.

Besides opening the nasal passages, an additional benefit from adding the mound 7 is that it spreads the cushion liner 5 laterally, which in turn reduces focalized pressure (commonly referred to as 'nose squeeze') of the cushion at the interface with the user's nose and/or face. This then improves user comfort and at the same time provides an equivalent or possibly a more evenly distributed and wider seal of the cushion liner 5 onto the user's face. In addition by doing that it improves cushion barrier adhesion around the user's face, thereby minimizing detrimental environmental influences from contacting the user's face and/or eyes, such as dirt, dust, snow, rain, and cold or hot air etc. This feature allows the user clearer vision for sporting activity, such as for motocross, where mud and dirt can accumulate inside the goggles and for snow related sports in which fogging of glasses can occur when snow and cold air cause water condensation inside goggles.

Figure 2:
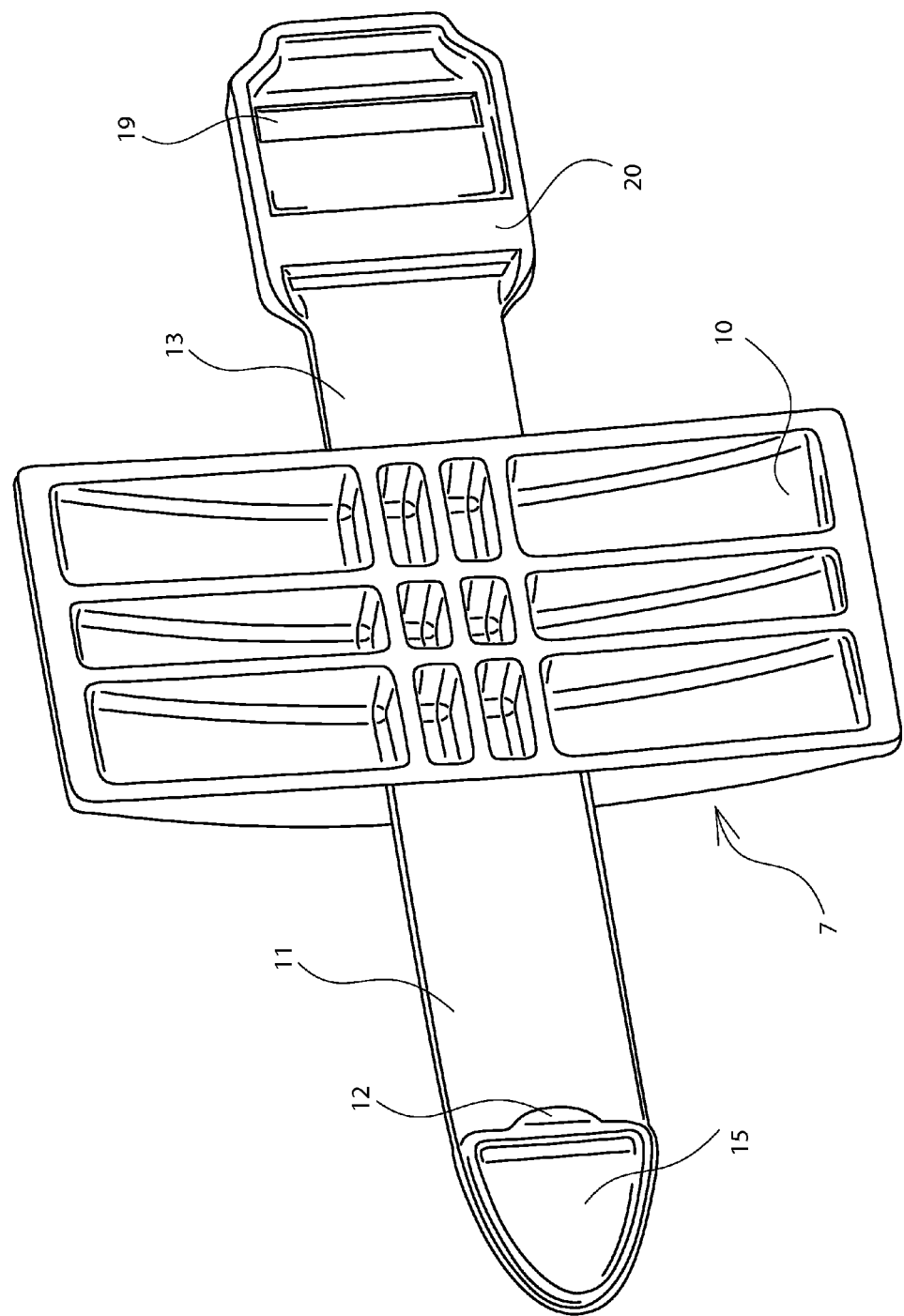
FIG. 2 shows the underside of the convex shaped dome mound in FIG. 1.

The shaped mound 7 as shown in FIG. 1, has a sloped-down configuration 9 on its anterior and posterior sides from its apex 8, creating a convex dome shape when viewed from the side. FIG. 2 shows the underside 10 of the mound 7. The dome shape fills in the anterior and posterior spaces created by tenting when the apex 8 of the mound 7 pulls the head retainer strap 4 away from the helmet 6 surface. Filling in these spaces is important to avoid foreign objects such as tree limbs from being caught inside those spaces. The holding means to keep the mound 7 in place is created by: (1) The inward pressure of the head retainer strap 4 onto the mound 7 and the interface between the mound and the helmet 6 or sides of the user's head; (2) addition of projections 14 on mound 7 around and/or on the apex 8 which interlock with the inner surface of the head retainer strap 4 and (3) by binding and tightening two mound straps 11, 13 around the head retainer strap 4. One method of binding mound straps 11, 13 together is interlocking mound strap 11 into a hole 19 on mound strap 13. When the mound straps 11, 13 are tightly bound around the head retainer strap 4, finger hold 15 of strap 11 is inserted through opening 19 and then pulled down and through loop 20, until abutment ridge 12 is in place to create an interference fitment locking means with loop 20, thereby preventing strap 11 from pulling back through loop 20. The surface of mound 7 with projections 14 that contact the head retainer strap 4 add holding means to prevent the mound 7 from sliding sideways or laterally along the head retainer strap 4. The interference fitment locking means 12, 20 and projections 14 are important for motorbike racers who need to place their goggles on just before a race begins and they need assurance that the mound 7 remains positioned optimally for nasal passage opening. The locking means for the mound straps 11, 13 can utilize Velcro or other methods known in the art, such as fitment of a projection(s) on strap 13 into a hole(s) in mound strap 11 (not shown).

The shape and size of the mound 7 can be configured to be any functional shape, such as rectangular but not limited to that shape and have variable heights (i.e. distance from apex 8 to bottom edge of mound). In an aspect the height can vary but not be limited between $1/10$ (0.1) inch to 1.0 inch. The ideal width of the mound 7 should be adequate to be covered by the width of most head retainer strap(s) 4, but the width of the mound 7 can be larger or smaller than the width of a head retainer strap 4. The mound 7 can be made of any suitable material with a durometer capable of maintaining the mounding effect to open the nasal passages.

There may be circumstances when a special height of the apex of the mound 8 may be required to achieve the functional effect to open nasal passages. One embodiment (not shown) would have add-on convex shaped plates like the mound 7 shown in FIG. 2 referred in this example as the base-plate mound 7 which could have for example an apex height of $1/2$ (0.5) inch and a 4 inch length created in part by the sloping anterior and posterior ends 9 of mound 7. The add-on plate would have the same convex shape as the base plate mound 7 without the side straps 11 and 13 and have no sides or internal structure except for a cylindrical protrusion on the underside of its apex. The base plate mound 7 would have a hole (not shown) near or at its apex so that the protrusion of the add-on plate would fit snugly into the hole on the apex of the base plate mound 7, thereby attaching and overlapping the base-plate mound 7 with the add-on plate. The add-on plate could have an apex height of $1/8$ (0.125) inch and a slope extension(s) 9 for example of an added 0.25 inch on each anterior and posterior end that would extend the total length of the mound now to 4.5 inches to compensate for the additional anterior and posterior opening created by the additional apex height of 0.125 inches. Hence the apex height of mound 7 can be adjusted by increasing or decreasing the add-on plates(s) as needed to achieve the most functional apical height for a particular user to achieve nasal opening wearing a helmet and goggle combination or a goggle.

Figure 3:
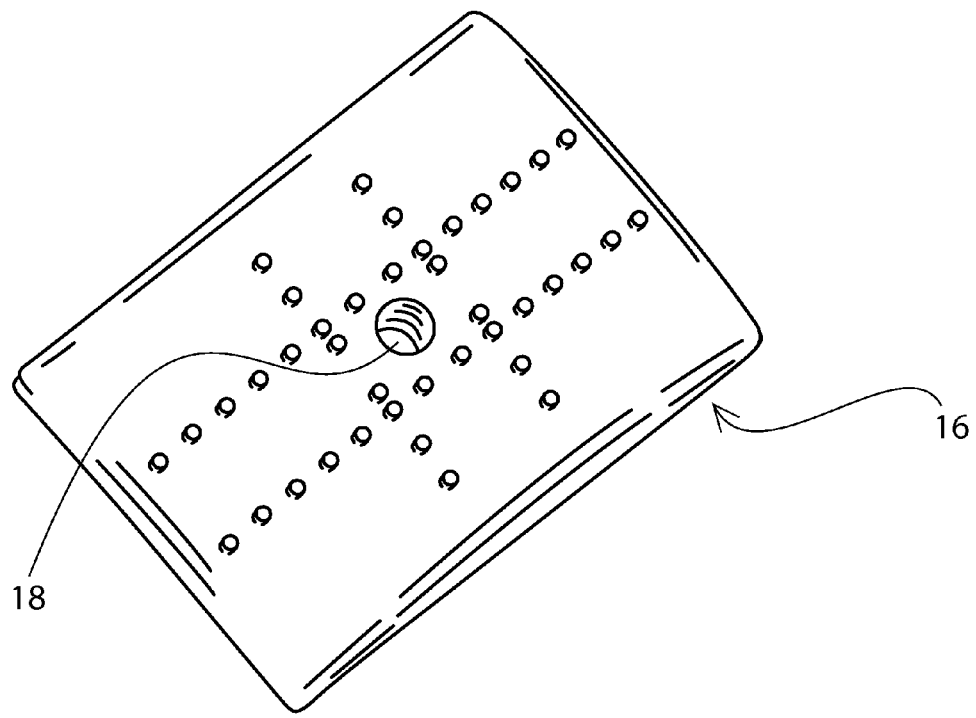
FIG. 3 shows the top view of an apex add-on segment that adds apical height when attached to mound illustrated in FIG. 1.
Figure 4:
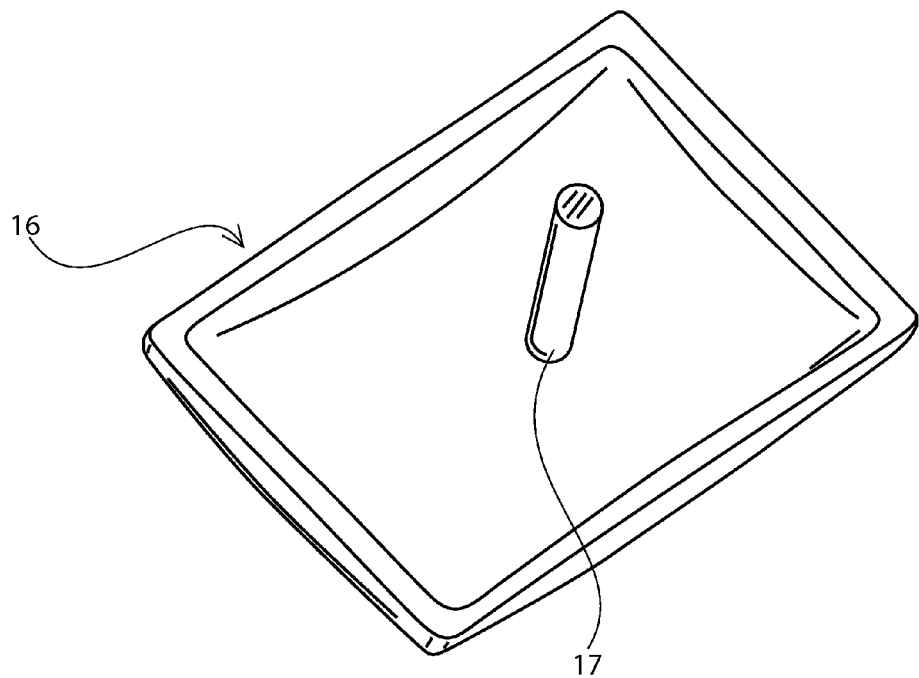
FIG. 4 shows the underside of an apex add-on segment shown in FIG. 3.

An apex add-on segment 16, FIGS. 3 and 4, can also be utilized. The add-on segments 16 could have for example a convex shape with an apex height of $1/8$ (0.125) inch height, with no interior supporting structure and sides, but with sloping anterior and posterior sides of a length shorter than the base plate mound 7 with slopes 9 shown in FIG. 1, for example $1/2$ (0.5) inch anteriorly and posteriorly. The apex add-on segment(s) 16 would have a protrusion 17 on its inferior surface which could fit snugly into a hole 18 located on the superior surface of the base plate mound 7 (not shown). The next apex add-on segment(s) would also have a protrusion 17 on its inferior surface that would fit into a hole 18 located on the prior apex add-on segment to allow stacking of the segments on each other. If needed, sloping segments could also be added with similar attaching means.

In yet another method of achieving nasal dilating effect, helmet 6 manufacturers can integrate a permanent mound on each side of the helmet to allow the head retainer strap 4 to stretch laterally over the mound to achieve the nasal dilator effect per the Cottle effect. The exterior surface of the mound can have a trough along its length to hold the head retainer strap onto the mound. Additionally, the helmet could have lips with overhangs along the longitudinal length of the mound to retain the head retainer strap 4 from moving off the mound(s).

In addition a dome shaped mound 7 could be a reversible or irreversible insert added to a helmet by an attaching means on the sides of the helmet. The attaching means can be any functional means known to those familiar with the art. An example of an attachment means integrated into the sides of the helmet, seen in FIG. 7 B, would be a longitudinal channel 101 formed in each side of the helmet. The channels have longitudinal rails 103 (seen in breakaway view) with lips 102 that gradually extend outwardly into a dome mound shape with sloping anterior and posterior ends. The rails 103 and lips 102 would be located above and below each other at a width that would accommodate the mound 7. The mound 7 could then slide onto the rails 103 of channel 101 with lips 102 fitting snugly over the superior and inferior sides of the mound 7, thereby locking and holding the mound 7 in place. Once the mound 7 is locked into place, then goggle retainer strap 4 would fit over the mound 7.

Additionally manufacturers can add a means to move the mound anteriorly and posteriorly on the sides of the helmet or in any other functional direction while contacting the inside of the goggles head retainer strap 4 to obtain the best effect for opening the nasal valves and/or nasal vestibules. For example (not shown) but not limited as such, two parallel rails can be added to each side of the helmet. The rails would have stops such as elevations in the rails that can be forcibly overridden. The mound would have grooves or other means to attach and ride on the rails and can be moved to any one of the designated stops. The mounds could be reversibly or irreversibly added or removed from the helmet.

Additionally as a different embodiment (not shown) it is possible to add mound(s) at strategic locations to the inside of a helmet which would apply stretch forces onto the user's face and could then pull the facial skin with its underlying anatomical attachments to open the nasal valves and/or vestibules.

Goggle manufacturers can also add an insert with mounds into the goggles to fit reversibly or irreversibly around or in proximity to the user's nose that will enhance nasal passage patency. In one aspect, soft and/or slightly compressible mounds can be added on the inside of the head retainer strap 4 at any propitious location to effect nasal dilation such as contacting the side of the user's head, or near the junction of the head retainer strap 4 with the housing 2 of the goggles 1. The mounds can be placed also on the cushion liner 5 and/or housing 2 of the goggles, such as near the nasal-facial junction or other locations on the user's cheek to obtain nasal dilation function pursuant to the goals of the present invention. Head retainer straps of some commercially available goggles may have loop Velcro on the inside of the head retainer straps 4, such that a soft mound with hook Velcro can attach onto the inside of the head retainer straps 4. According to this nasal dilator accessory embodiment, the soft mounds can be of different heights and shapes depending on the user's facial configuration in order to open the nasal valves and/or nasal vestibules, and they can be made of different materials such as thermoplastics, non-latex rubber, neoprene, polyurethane, textiles, silicone and other similar soft materials, each of which are non-limiting embodiments of the invention. As mentioned, the mound(s) can be manufactured with integration into the goggles head retainer strap 4 or be made to strap around the head retainer strap 4 and/or have a slot means through which to slide the mound onto the head retainer strap 4. Mound additions to goggles for nasal dilation can be used for many activities, such as for skiing, snow-boarding, snow-mobiling, contact sports and tactical military uses.

In another embodiment of adding a mound to the goggle head retainer strap, manufacturers could utilize a bladder (not shown) capable of filling up with air or liquid or other suitable filling material added to an opening in the bladder that can be closed off, or be pumped in through a valve. As air or liquid or suitable filling material is introduced into the bladder it could balloon up to a shape similar to mound 7, but could also be any functional shape to create a mound 7 effect, and could have straps 11 and 13 on each side for attaching to the goggle head retainer strap 4. The apex height and sloping ends would increase depending on the amount of air, liquid or other suitable filling material introduced into the bladder. A pouch or pocket could be created on the goggle head retainer strap 4 to position the bladder type of mound 7. In addition the bladder can be manufactured so that it is integrated into the head retainer strap.

Goggle manufacturers could also add ledge extensions to the lateral sides of the housing 2 for attachment of the head retainer strap 4. This would cause more stretch of the head retainer strap 4 laterally on the user's head and thereby create lateral stretch forces that are transmitted onto the cushion liner 5 to improve nasal patency. In this embodiment no mound is needed but the goggles with the ledges still have the same functionality as other described iterations of the invention described herein. They are reusable, re-adjustable and re-locatable and have the varying tightening means of the head retainer strap 4, so that when activated, cause lateralizing and other vectored forces to be transmitted onto the cushion liner 5 and thereby onto the user's face and skin. This then accomplishes the Cottle effect to open the nasal valves. However this embodiment adds a risk of head injury to a rapidly moving user if a tree limb or other foreign object gets entrapped into the space created posterior to the ledge extension between the sides of the user's head and the head retainer strap 4. As such a filler of any soft, semi-rigid or rigid material would need to be integrated or attached as an accessory to the posterior side of the ledge extension(s) and then slope down distally to fill the gap between the head retainer strap 4 and the anterior part of the helmet. If the goggles were used by themselves without a helmet, the filler would need to be made of a softer material as it would approximate the user's head.

In another aspect, some protective goggles (also known as eyewear) 21 used mostly for contact sports but occasionally for non-contact sports, FIG. 7 C, have many of the same features as ski and motorbike goggles 1. They have a rigid or semi-rigid housing 2 with a bridge 3 that is located above and/or over the user's nose, a partial or full cushion 5 to contact the user's face and adjustable elastic retainer straps 4 and they contain clear eye barriers 100 as part of the housing 2. The housing 2 in these applications can also be manufactured so they are integrated with eye barriers as one part. Some have partial or full temples 22 that are connected to the housing 2 but in this application, temples are considered to be part of the housing 2. Hence describing attachment of a head retainer strap 4 to a housing 2 can mean attachment directly to a housing 2 and/or to temples 22 as part of the housing 2. In these applications, a mound 7, preferably using a soft material with some compressibility since they will be in direct contact with a user's head, can be added to effect nasal dilation. When used in this application, the mound 7 can be added to the adjustable retainer strap 4 or to the housing 2 with or without temples 22 causing the skin underlying the mound 7 to be pulled to open nasal valves per the lateralizing vector of the Cottle effect and also by lateral-superior vector forces posterior to the lateral canthi. The mound 7 can be any functional shape and attached to adjustable head retainer straps 4 for example with mound straps 11, 13 or slipped over and/or around the head retainer straps 4 as with the swim goggles 36 seen in FIGS. 9 A to 9 E. Additionally, the mound 7 can also be integrated into the manufacture of the head retainer strap 4 or temples 21.

As described herein, the components of goggles alone or a combination of goggles with a helmet, including a mound(s) 7 added to either goggles or a helmet, have all Essential Elements according to the invention for a nasal dilator device, including: (1) a rigid or semi-rigid housing 2 with a bridge 3 providing means for maintaining adjusted forces for nasal dilation for either or both sides of user's nose; (2) the bridge 3 as part of the housing, located above and/or over the nose to distribute nasal dilating forces to either or both sides of a user's nose and/or face; (3) mounds 7; (4) a holding means for mounds 7 on goggles head retainer strap using mound straps 11,13 and the inward pressure of goggles head retainer strap 4 holding mound 7 onto helmet 6 or head of a user to maintain positioning of mounds; (5) means for attachment of tightening means, i.e. goggle head retainer strap 4 attached to housing 2; (6) capability of changing and varying tightening means, i.e. goggle head retainer straps 4, onto mounds 7 to open nasal passages i.e. nasal valves and/or nasal vestibule; (7) ability to adjust, and/or relocate mound(s) 7 to same or different location(s) in relation to user's nose, face and/or head as needed to improve nasal patency and/or patient comfort; and (8) reusability.

Although the nasal dilator is the primary function for this application, it also provides an additional advantage by spreading the cushion liner 5 laterally, reducing focalized pressure around the user's eyes and nose and thereby improve user comfort while wearing goggles, and improve cushion barrier adherence onto and around user's face against entry of detrimental environmental influences, such as dirt, snow, rain, cold air and the like. As referred to herein throughout the application, detrimental environmental influences are intended to be blocked or sealed away from at least a portion of the user's eyes, nose and/or face.

Nasal Dilating Device Application for Swim Goggles with or without a Swim Cap.

Figure 8:
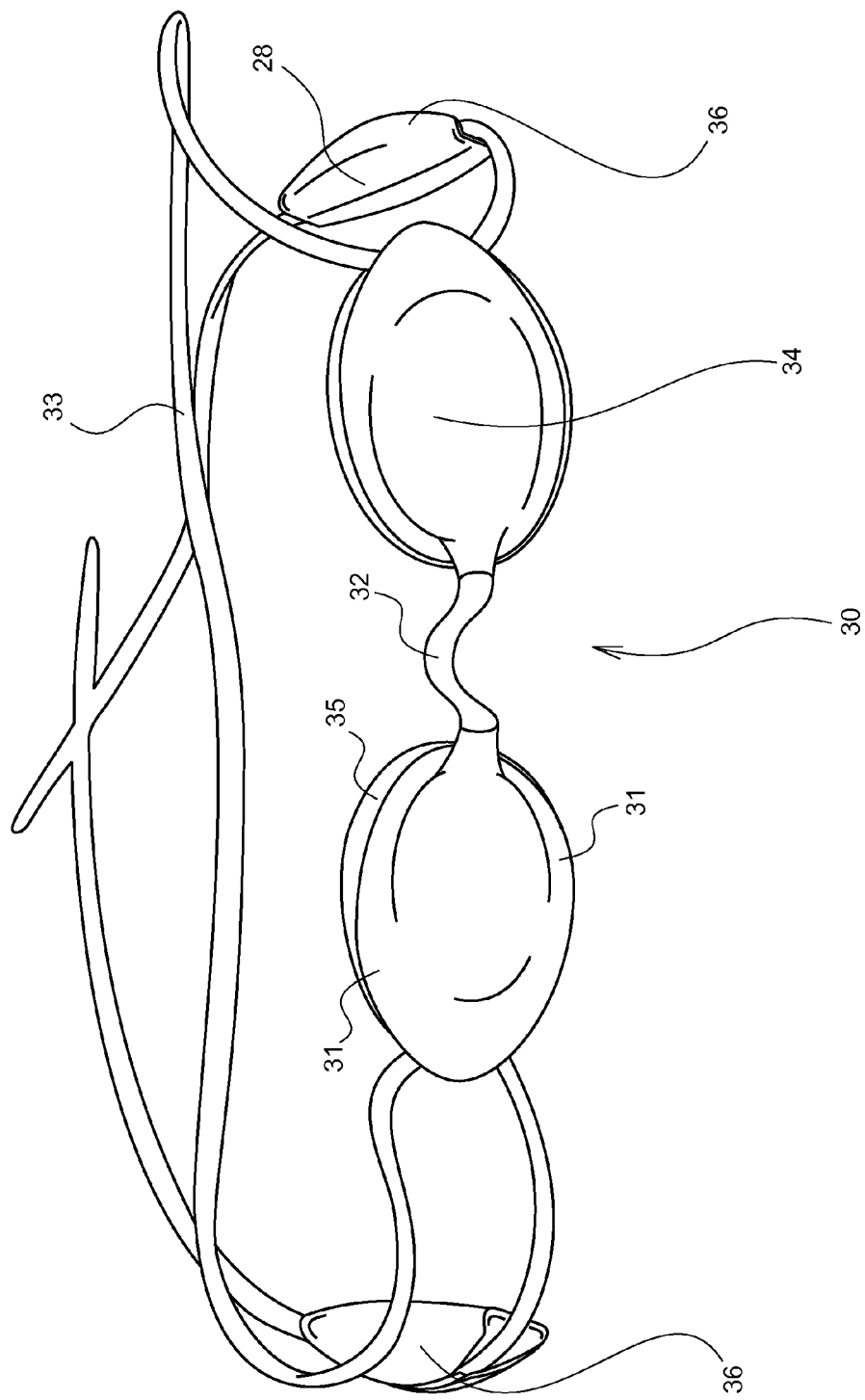
FIG. 8 shows front view of swim goggles with mound seen in FIG. 9 D attached to swim goggle straps, according to an embodiment of a nasal dilator device for this application.

Swim goggles 30 have structure similar to goggles 1 used for winter and dirt biking activities. FIG. 8 shows swim goggles 30 with: a rigid or semi-rigid housing 31 that has a bridge 32 located above and/or over the user's nose and housing rims (also can be referred to as eye cups) 31 to hold a translucent barrier 34 to protect the user's eyes; a soft cushion liner 35 attached to the rim part of housing 31 which interface the user's face when worn; and a tightening means in the form of swim goggles head retainer straps 33 attached to the housing 31.

Swim goggles basic function is to protect the swimmer's eyes from water irritation by preventing leakage of water into the goggles. In addition ideally swimmers can improve their capability and endurance by breathing effectively through their nose. Nevertheless some swimmers cannot effectively do that because they have faulty nasal valves or other confounding internal nasal anatomy to preclude normal patency of the nasal passages. The selective addition of mounds 36 to this application improve opening of nasal passages so that the user can more easily breathe through their nasal passages. Mound(s) 36 can be added by slipping into and/or onto the swim goggle straps 33 located on the sides of the user's head or at any location on the swim goggle straps 33 that are attached to the housing 31, such as close to the rims or along the lateral or posterior aspects of the swimmer's head. Mounds 36 can be any shape that provide an increased apical lateral height when attached to swim goggle straps which in turn stretch the goggle straps in a lateral vector. Mounds 36 can be dome or torpedo-like shape to reduce water resistance and a flat side 28 to approximate user's head comfortably and improve stabilization of the mound 36 when placed onto the user's head, FIGS. 9 D and 9 E. It can have a groove or slit 38, FIG. 9B, on its exterior side to allow the swim goggle straps to be enclosed inside the mound 36 and also allow the mound 36 to slide anteriorly or posteriorly on the lateral side of the user's face for optimal functional location. This embodiment can also be made without a groove but with a channel 39, FIG. 9C, to allow the mound 36 to slip through the ends of the swim goggle strap 33.

Figure 9:
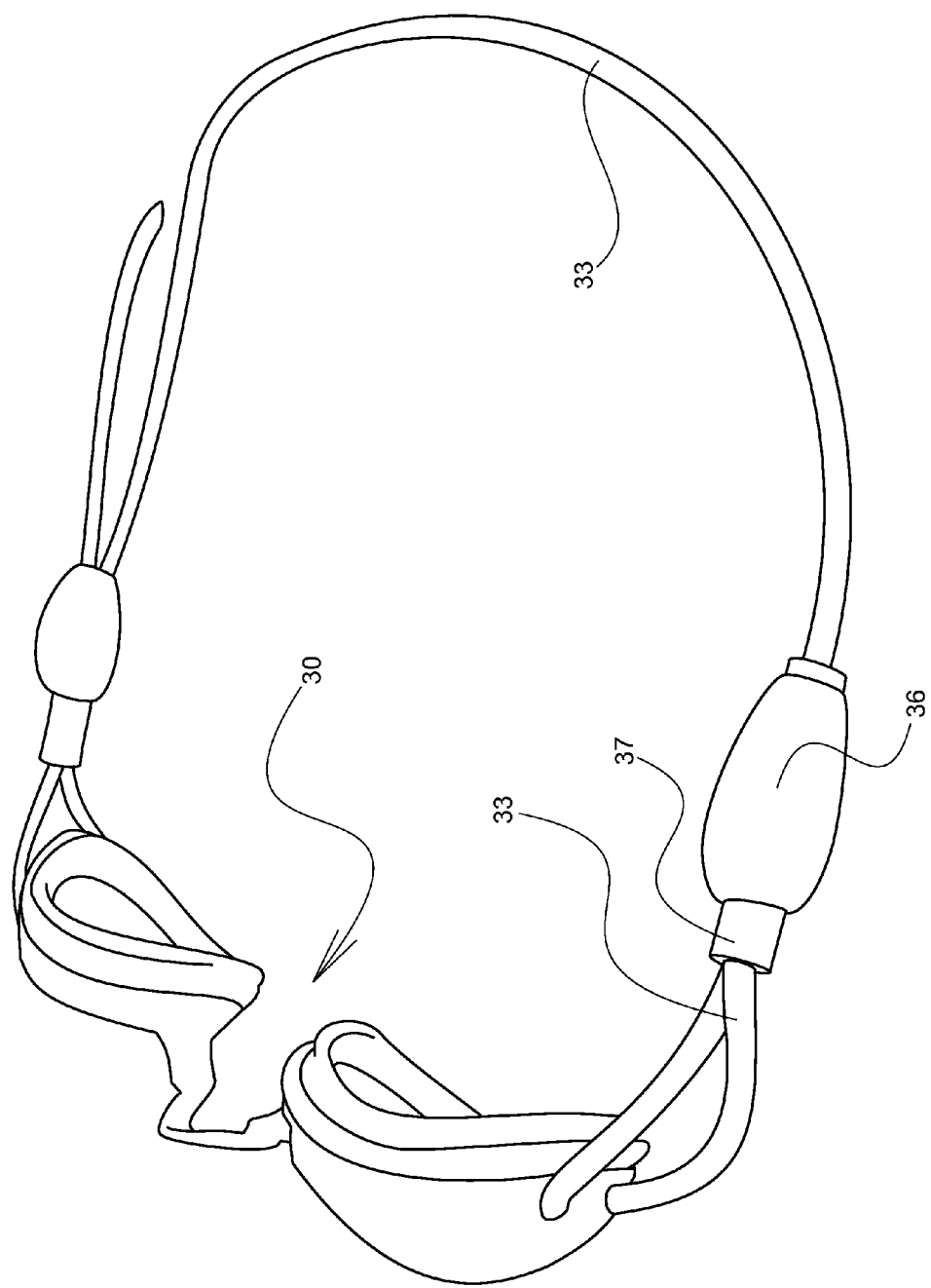
FIG. 9A shows swim goggle straps with attached mound comprised of a rigid or semi-rigid cylindrical part with a soft compressible exterior, according to an embodiment of a nasal dilator device for this application.
FIG. 9B shows a cross section of eccentric shaped mound with a slit that can be situated onto swim goggle straps, according to an embodiment of a nasal dilator device for this application.
FIG. 9C shows an eccentric shaped mound with a channel that can be situated onto swim goggle straps, according to an embodiment of a nasal dilator device for this application.
FIG. 9D shows a cross section of a mound to be attached to swim goggle straps, comprised of a slit aperture and a floor to accommodate most sizes and shapes of goggle straps, according to an embodiment of a nasal dilator device for this application.
FIG. 9E shows a top perspective of swim goggles with mound embodiment seen in FIG. 9 D showing overlapping flaps of mound attached to swim goggle straps, according to an embodiment of a nasal dilator device for this application.
Figure 9:
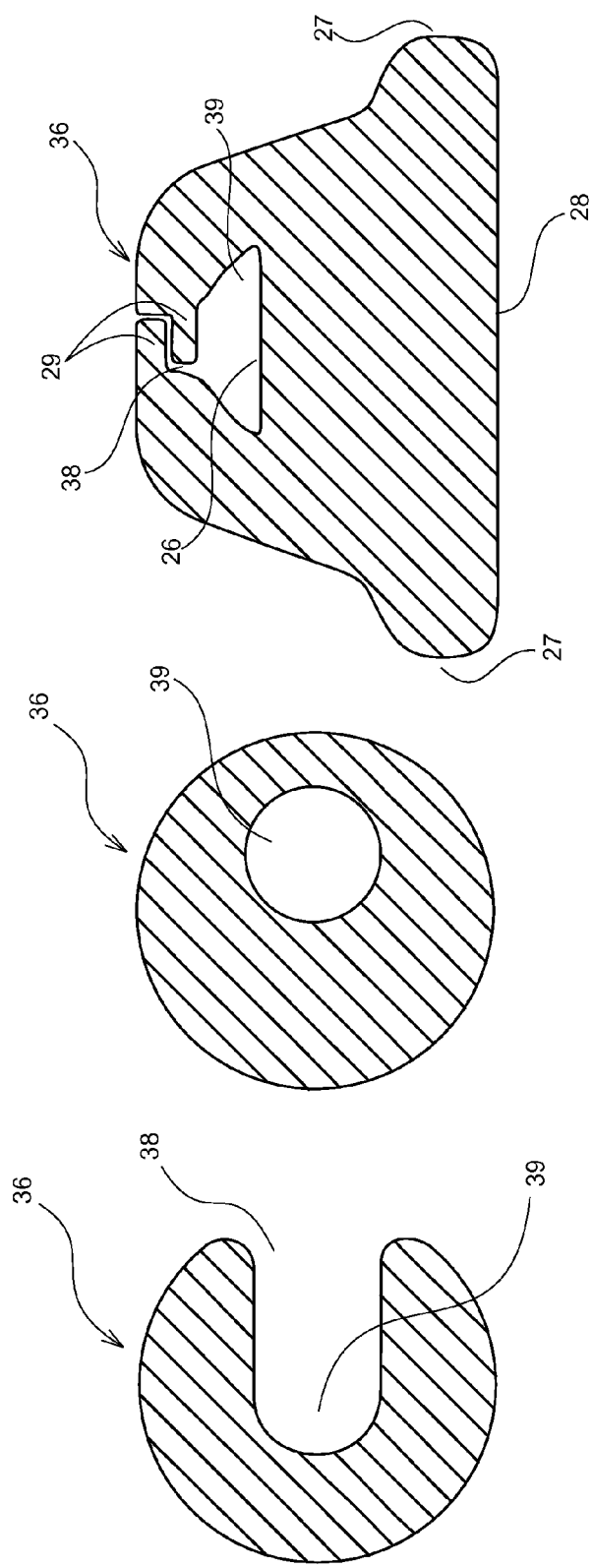

Mounds 36 can also be concentric or eccentric shaped with transitional radius widths that enclose a channel 39, FIG. 9C, or enclose a longitudinal channel 39 with a longitudinal slit opening 38, FIGS. 9 B and 9 D. The mounds 36 with channels 39 can be slipped through the ends of swim goggle straps 33, FIG. 9 C and positioned as needed for functionality or they can have longitudinal slits 38, FIGS. 9 B and 9 D, to allow the goggle straps 33 to snap into the channel 39 of the mound 38. Eccentric mounds, FIGS. 9B and 9C, can be rotated to obtain the optimal radius width to create nasal dilation. Mounds 36 can also have shapes like a 'U' that can be slipped around the goggle straps 33. The mounds have the following holding means: (1) being slipped into and/or onto around swim goggle straps 33; and (2) positioning of the mound 36 between the user's head and the mound 36 that is attached to goggle straps 33. The force of the tightening means 33 onto the mound(s) 36 can be varied by loosening or tightening the swim goggle head retainer straps 33 around the swimmer's head and/or by rotating the radius width of an eccentric shaped mound 36, FIGS. 9 B and 9 C, between the goggle straps 33 and the user's head.

The mounds 36 increase the moments of forces vectored mostly laterally and posteriorly but also superiorly and inferiorly onto the cushion liner 35, around the user's eyes, nose and face and thereby onto the underlying skin and anatomical attachments to open the nasal valves/vestibule. Most of the vectored pull with the mounds occur above and below the lateral canthi of the eyes. The rigid or semi-rigid housing 31 with a bridge 32 provides means for maintaining adjusted forces for nasal dilation to either or both sides of user's nose. The lateralizing forces of the mound 36 also cause the cushion liner 35 to spread laterally and by doing so, reduce the medial and posterior pressure around the user's eyes, called eye squeeze as well as nose squeeze, and at the same time maintain or improve the water seal of the cushion liner around the swimmer's face. Changing the tightening of swim goggle head retainer straps 33 is often time consuming and frustrating so that addition of mound 36 may obviate the need to adjust the tightening of swim goggle head retainer straps 33, particularly if adjustment is needed because of water leakage into the user's eyes. An advantage of the eccentric mound 36 described above with a channel 39, FIG. 9 C, or a slit, FIG. 9 B, for attachment to swim goggle head retainer straps 33, is it can allow the user to rotate the mound 36 to obtain the optimal radius width between the mound 36 and the user's face to achieve the functions of opening the nasal passages and/or reduce leakage between the cushion liner 35 and the swimmer's face and eyes and/or reduce eye or nose squeeze.

The potentially preferred embodiment of the mound 36 added to goggle head retainer straps 33 is shown in FIGS. 9D and 9E. The mound 36 is dome or torpedo shaped to reduce water resistance and has a flat side 28 that contacts the user's face when added to the swim goggles 33. The goggle straps 33 are placed through slit 38 which is bordered by flaps 29 that can oppose each other or overlap each other to keep the straps from slipping out of the mound 36. The interior of the mound 36, FIG. 9 D, has a compressible or non-compressible floor surface 26 onto which the goggle straps contact. Extensions 27 can be added laterally to the flat side 28 of the mound 36 to stabilize the positioning of the mound 36 on the user's head. This embodiment will accommodate most shapes and sizes of goggle straps 33.

Another embodiment seen in FIGS. 9 A, can include a rigid or semi-rigid concentric or eccentric cylindrical or other shaped structure 37, either with or without a slit. These semi-rigid or rigid structures 37 can slip around the swim goggle straps 33 if a slit 38 is part of their design or slip over the ends of swim head retainer goggle 33 through a channel 39. A soft mound 36 that contacts the user's face, like a water repellant layered gel, can be added to the rigid or semi-rigid structure 37 using an adhesive on the underside of the gel or other attaching means or be molded together with the rigid or semi-rigid cylindrical part 37. The combination of a rigid or semi-rigid structure 37 with a soft mound 36 can be manufactured as a single integrated eccentric or concentric unit and then be added to the swim goggle head retainer straps 33 by slipping through the slit opening 38 in the integrated unit around the straps 33 or by slipping the integrated unit through the ends of the swim goggle head retainer straps 33. The rigid or semi-rigid structure 37 will permit easier rotation and/or longitudinal movement of the soft mounds 36 on the swim goggle head retainer straps 33 and the eccentric embodiment allows for change in radius widths to approximate the user's face and optimize nasal passage opening.

Figure 10:
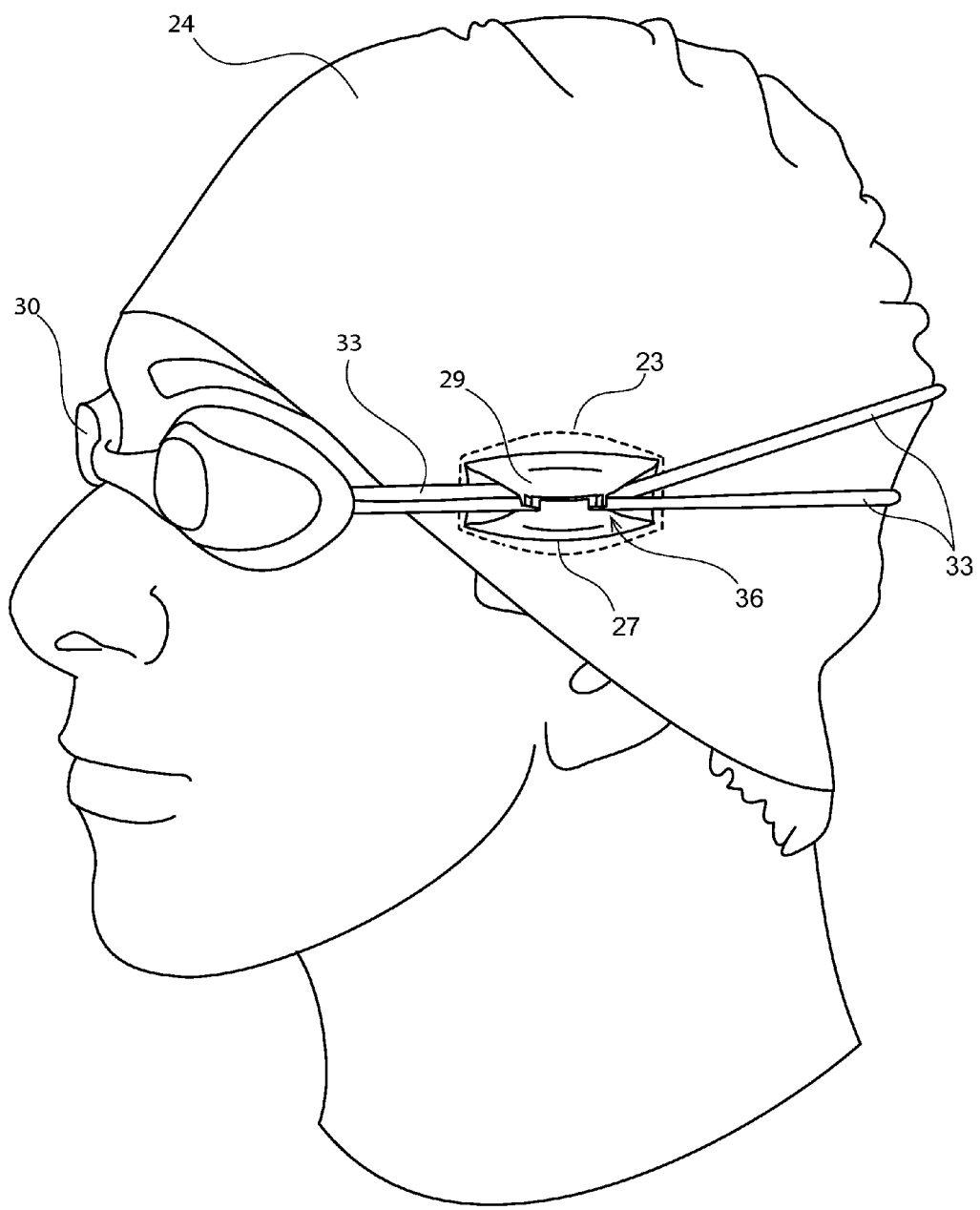
FIG. 10 shows a swim cap with a break away view of a mound seen FIG. 9D, according to an embodiment of a nasal dilator mound device for this application.
Figure 11:
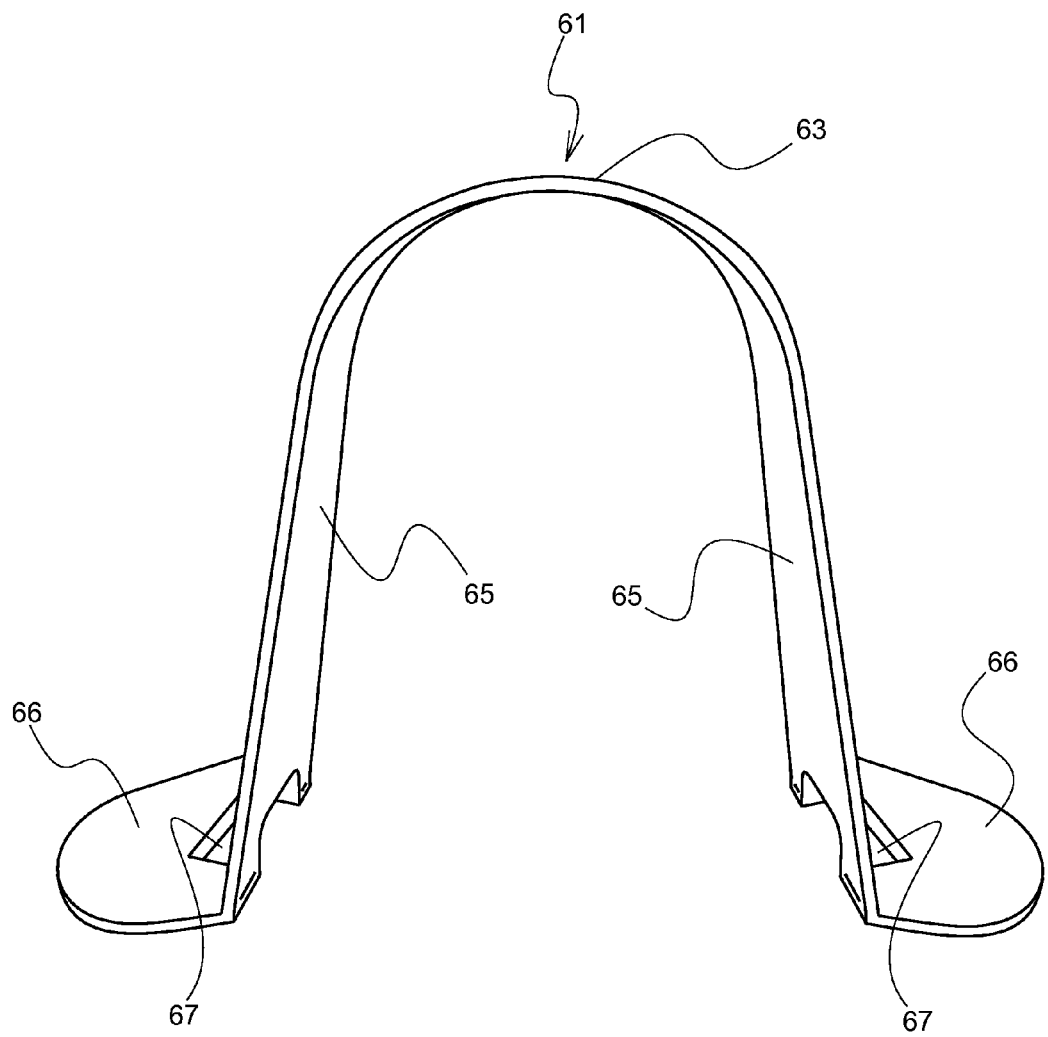
FIG. 11 shows a rigid or semi rigid housing for a hybrid sleep mask according to an embodiment of a nasal dilator device for this application.
Figure 12:
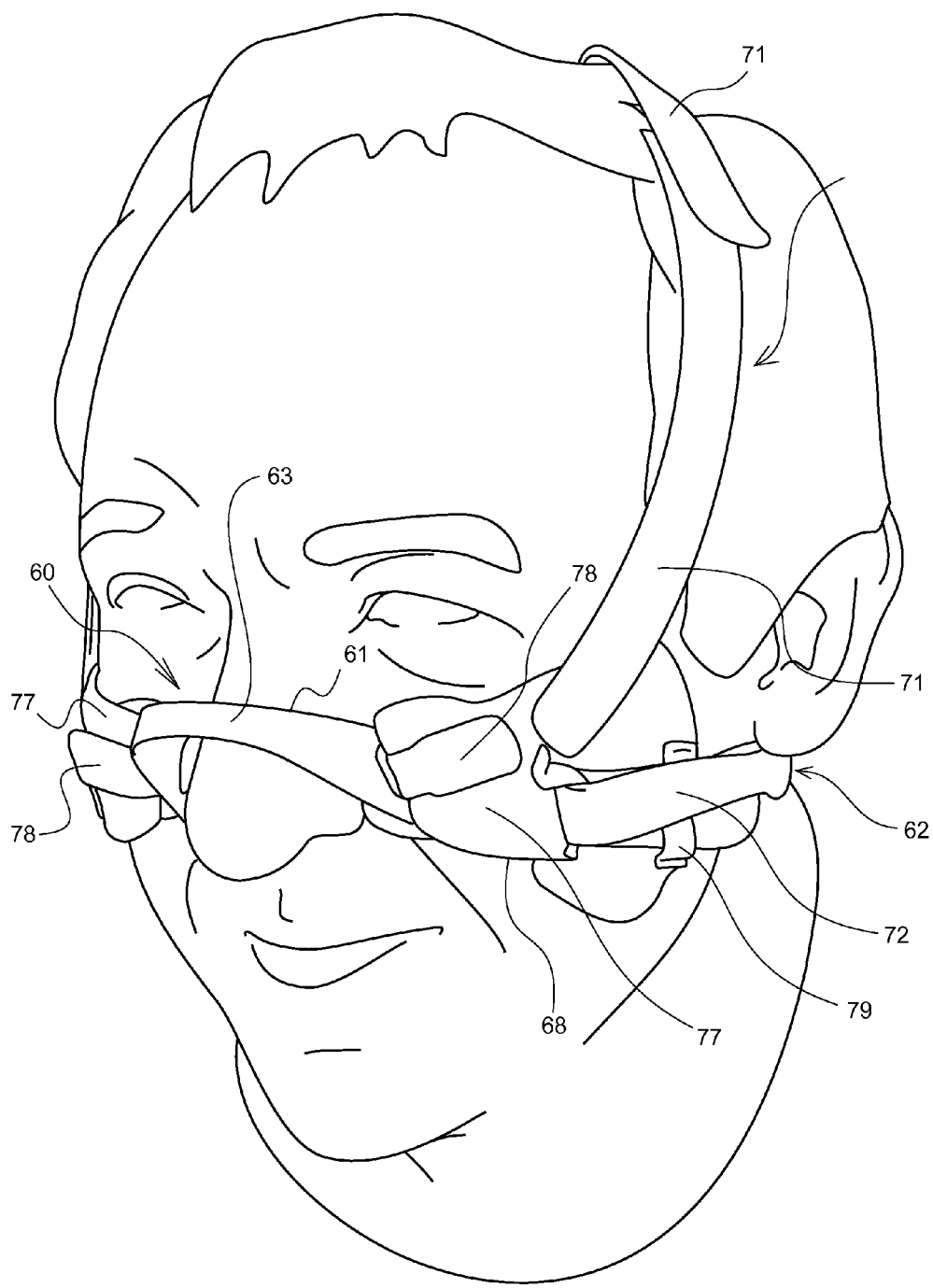
FIG. 12 shows a hybrid sleep mask on a user comprising a rigid and/or semi-rigid housing in combination with a stretchable or non-stretchable component, according to an embodiment of a nasal dilator device for this application.
Figure 13:
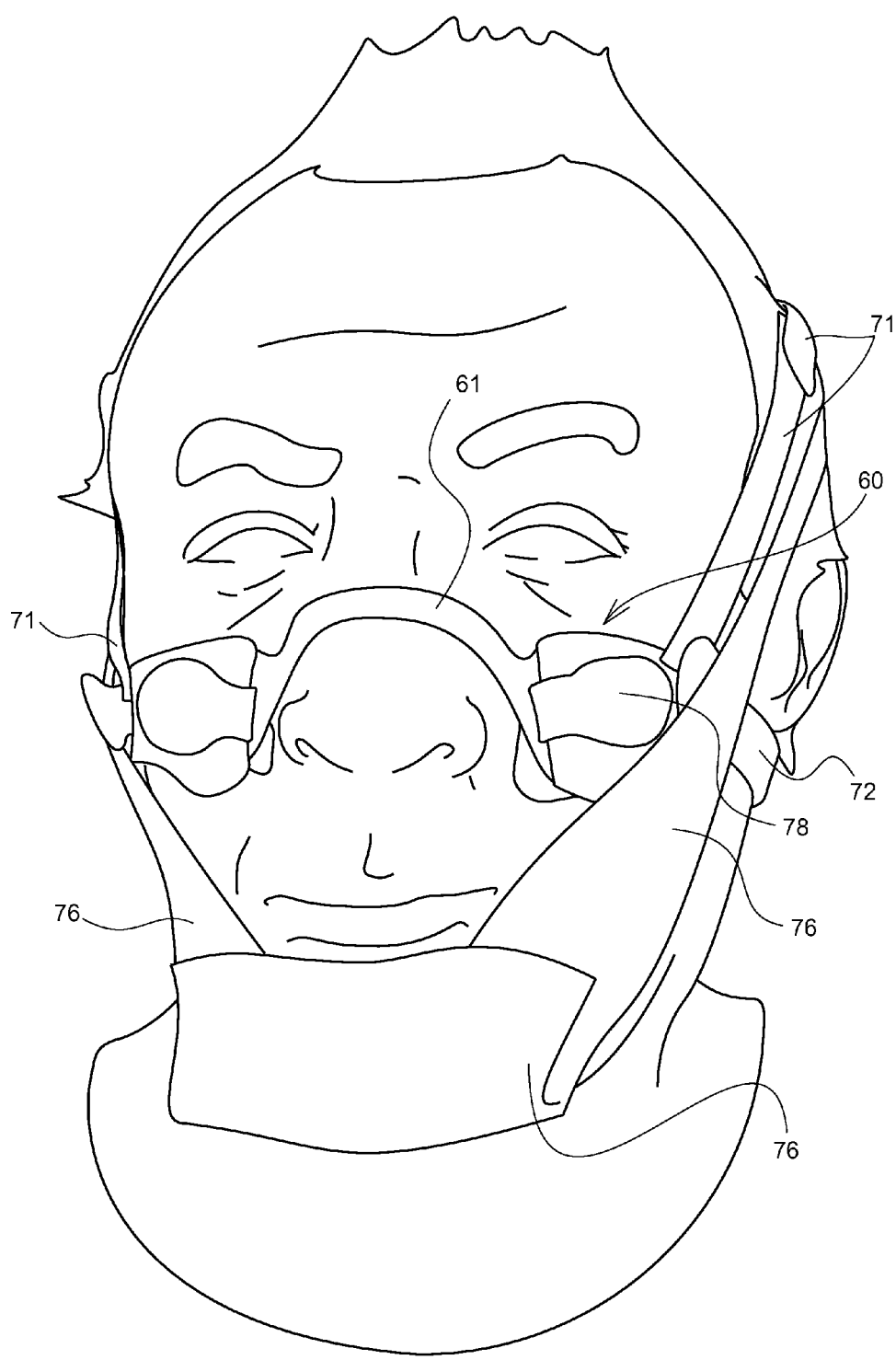
FIG. 13 shows a hybrid sleep mask on a user with chin support, according to an embodiment of a nasal dilator device for this application.

In yet another embodiment, as shown in FIG. 10, a mound 36 could be added as an accessory or integrated into a swimmer cap 24. For example without limitation, an opening 23 can be added to the swim cap 24 and the mound 36 can be attached through the opening 23 as an accessory using adhesives or other attaching means to the inside of the opening 23. The flat extensions 27 would overlap the inside of opening 23 so that the mound 36 exteriorizes to the outside of the swim cap 24. The goggle head retainer straps 33 then fit inside the mound 36 with its flaps 29 covering the goggle head retainer straps 33 to maintain their positioning on the cap 24. The mound 36 can also be integrated into the manufacture of the swim cap and then the goggle head retainer straps 33 are placed into the mound 36. When the swim cap is worn, the mound 36 will create lateral posterior and/or superior vectored forces onto the goggle straps 33. In turn those forces are transmitted onto the cushion liner 35 approximating the user's face and eyes and underlying skin especially posterior to the lateral canthi, and then to underlying anatomical connections to the nose. This results in opening the nasal passages and at the same time relieves some of the eye and/or nose squeeze associated with wearing swim goggles because the cushion moves laterally and posteriorly of the lateral canthi. Manufacturers can also integrate the manufacture of mounds to swim goggle head retainer straps 33 or to the cushion liner 35 around the swimmer's nose or to other locations on the cushion liner 35 or housing 31 where the mound contacts the swimmer's face.

As described herein, the components of swim goggles used alone or in combination with a swim cap, both including mound(s) 36, have all Essential Elements according to the invention for this application of a nasal dilator device, including: (1) a semi-rigid or rigid housing 31 with a bridge 32 providing means for maintaining adjusted forces for nasal dilation for either or both sides of user's nose; (2) the bridge 32, that is part of the housing, located above and/or above the nose to distribute nasal dilating forces to either or both sides of a user's nose and/or face; (3) mound 36 located on swim goggle head retainer straps 33 or with a swim cap 24; (4)

holding means for mound 36 attached to swim goggle head retainer straps 33 and holding means created by interfacing of mound 36 with user's face and/or head; (5) means for attachment of tightening means, i.e. swim goggle head retainer straps 33 to housing 31; (6) capability of changing and varying tightening means such as swim goggle head retainer straps 33, onto mounds 36 to open nasal passages i.e. nasal valves and/or nasal vestibule and/or rotation of eccentric mound 36 to change radius of mound between user's head and mound 36; (7) ability to adjust, and/or relocate mound 36 to same or different location(s) in relation to user's nose, and/or face and/or head as needed to improve nasal opening; and (8) reusability.

Although the nasal dilator is the primary function for the swim goggles application, it also provides additional advantages by creating increased moments of forces onto the cushion liner 35, which: (1) spreads cushion liner 35 laterally to improve adherence of cushion liner 35 with user's face and thereby reduce leakage between the cushion liner 35 and the swimmer's eyes and face; and (2) spreads cushion liner 35 laterally thereby reducing the pressure or squeeze around the user's eyes and/or nose.

Nasal Dilating Device Application for a Hybrid Mask Used for Sleep and/or Exercise Comprised of Rigid and/or Semi-Rigid Housing and Stretchable and/or Non-Stretchable Material.

In another aspect, the nasal dilator devices used to open nasal valves and/or vestibules are referred to in this application as a hybrid sleep mask but it can also be used for exercise activities. It is comprised of a rigid and/or semi-rigid housing with stretchable or non-stretchable mask material 62, as depicted in FIGS. 11 through 17. As suggested by the nomenclature, this nasal dilating device for a hybrid sleep mask application 60 is comprised of a semi-rigid or rigid housing 61, FIG. 11, in combination with a stretchable or non-stretchable component 62, seen in FIGS. 12 through 16. The housing 61 is comprised of a bridge 63 with an opening 64 that is positioned over the user's nose. The housing has extensions 65 which are located on both sides of the user's nose. In addition the inferior ends of the extensions 65 have foot pads 66 with opening 67 for integration with the stretchable or non-stretchable material 62. The bridge 63 can be located directly in line with the extensions 65 or it can angle forward anteriorly/or posteriorly at any angle to the line of the extensions 65.

The arch of the bridge 61 and the extensions 65 of the bridge can be made so they can be adjusted regarding the width of the arch of bridge 63 or the length of the extension(s) 65 respectively. Although not shown, these embodiments could require complementary parts with means for their attachment, such as holes in one complementary part of an arch or extension and protrusions in the other complementary part of the arch or extension(s). This would then allow the complementary parts for the arch from opposite sides to connect by inserting the protrusions into the holes for optimal arch width. Each extension would have two complementary parts, one with holes and the other with protrusions, such that when the optimal length of the extensions are determined, then the protrusions would be inserted into the holes. The complementary parts would be designed and made of semi-rigid or rigid materials to permit reversibility of the attaching means involving the protrusions into holes, thereby permitting optimal dimensions for each user's facial configuration.

In one embodiment there is a pocket 77 formed in the stretchable or non-stretchable material 62 to allow the foot pad 66 to be inserted and enclosed in the pocket 77. The stretchable or non-stretchable component 62 comprise pocket straps 78, FIGS. 12 and 13, with Velcro or other attaching means to pull through the opening 67 in foot pad 66 and in turn attach the foot pad 66 inside the pocket 77. The same material that makes the pocket 77, creates a mound 68 on the medial side of the foot pad 66, FIG. 16, which will contact the user's face on both sides of the nose and cheeks. The stretchable or non-stretchable component 62 permit adjustable tightening straps 71, 72 to fit many different facial and head configurations.

Figure 14:
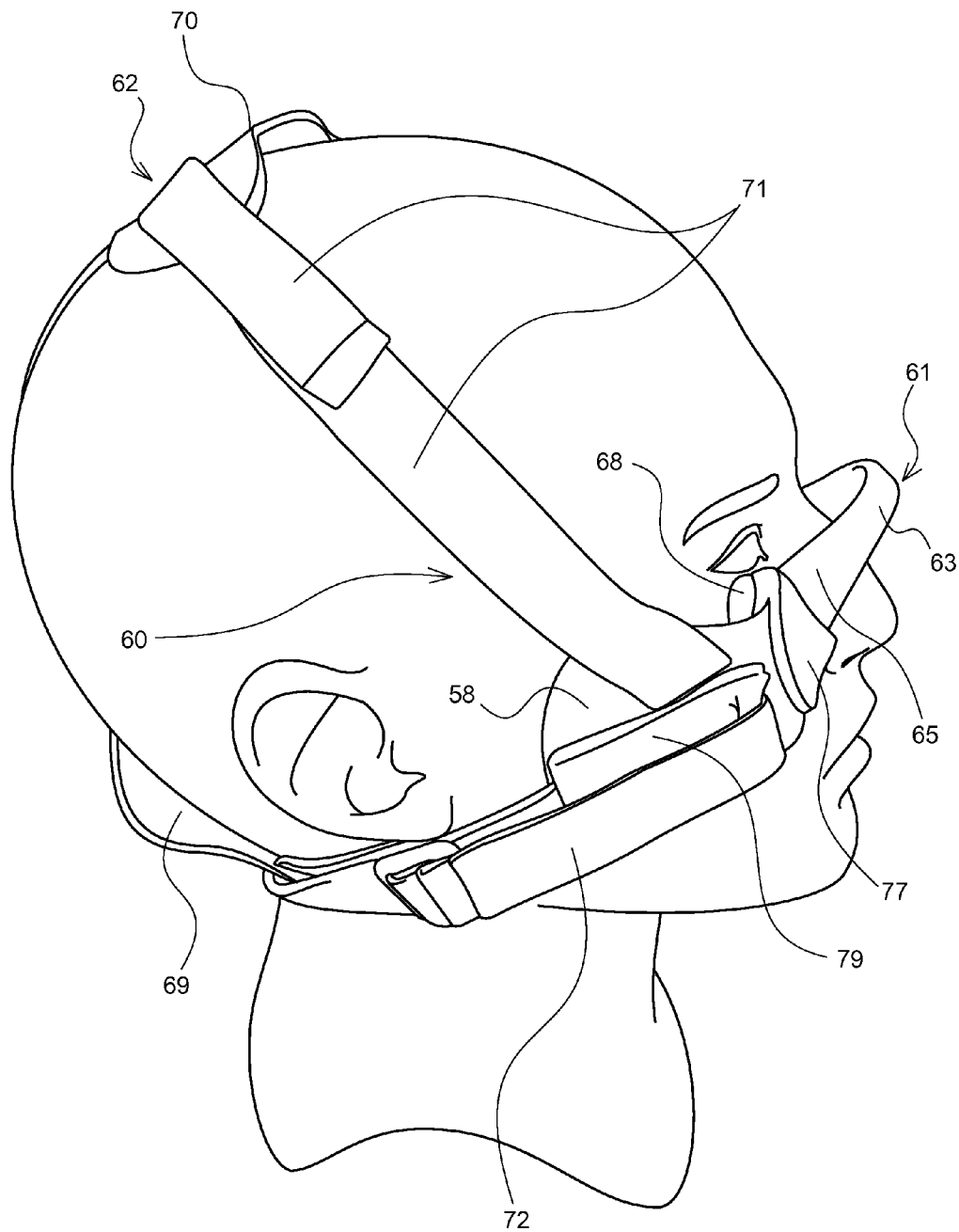
FIG. 14 shows a side perspective of a hybrid sleep mask, according to an embodiment of a nasal dilator device for this application.
Figure 15:
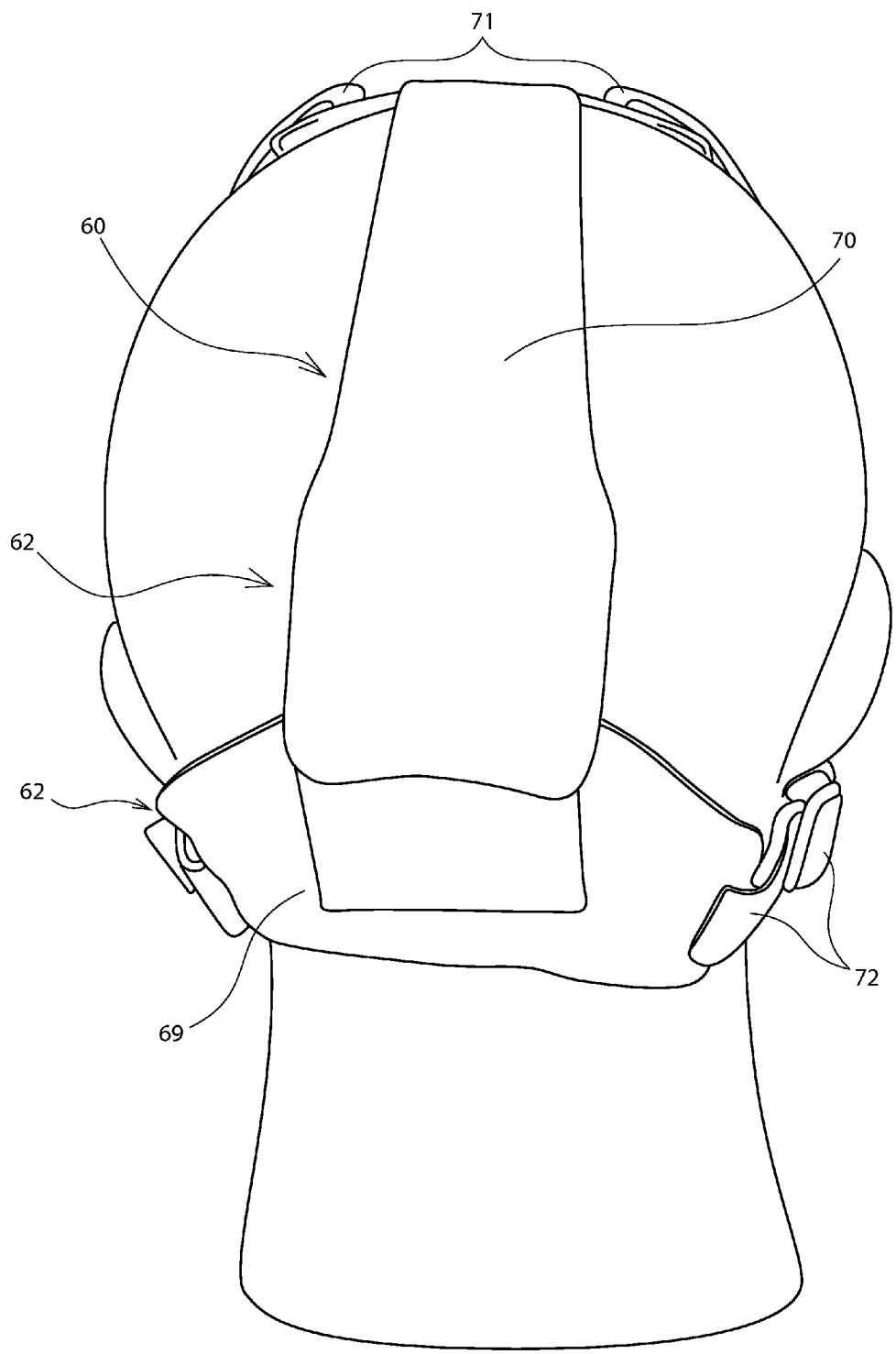
FIG. 15 shows a posterior perspective of a hybrid sleep mask, according to an embodiment of a nasal dilator device for this application.
Figure 16:
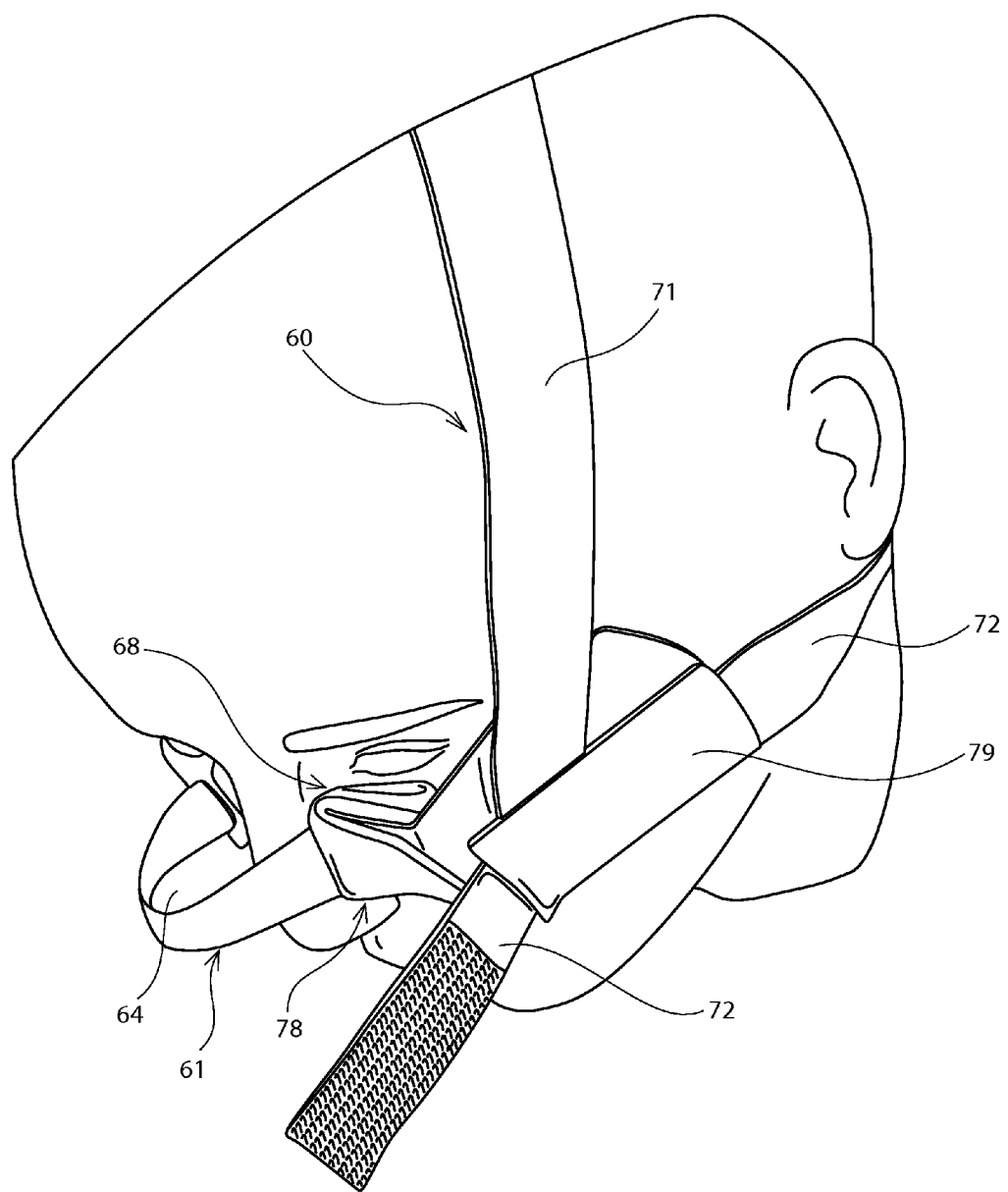
FIG. 16 shows a close up of a superior-lateral side perspective of a hybrid sleep mask on a user, according to an embodiment of a nasal dilator device for this application.
Figure 17:
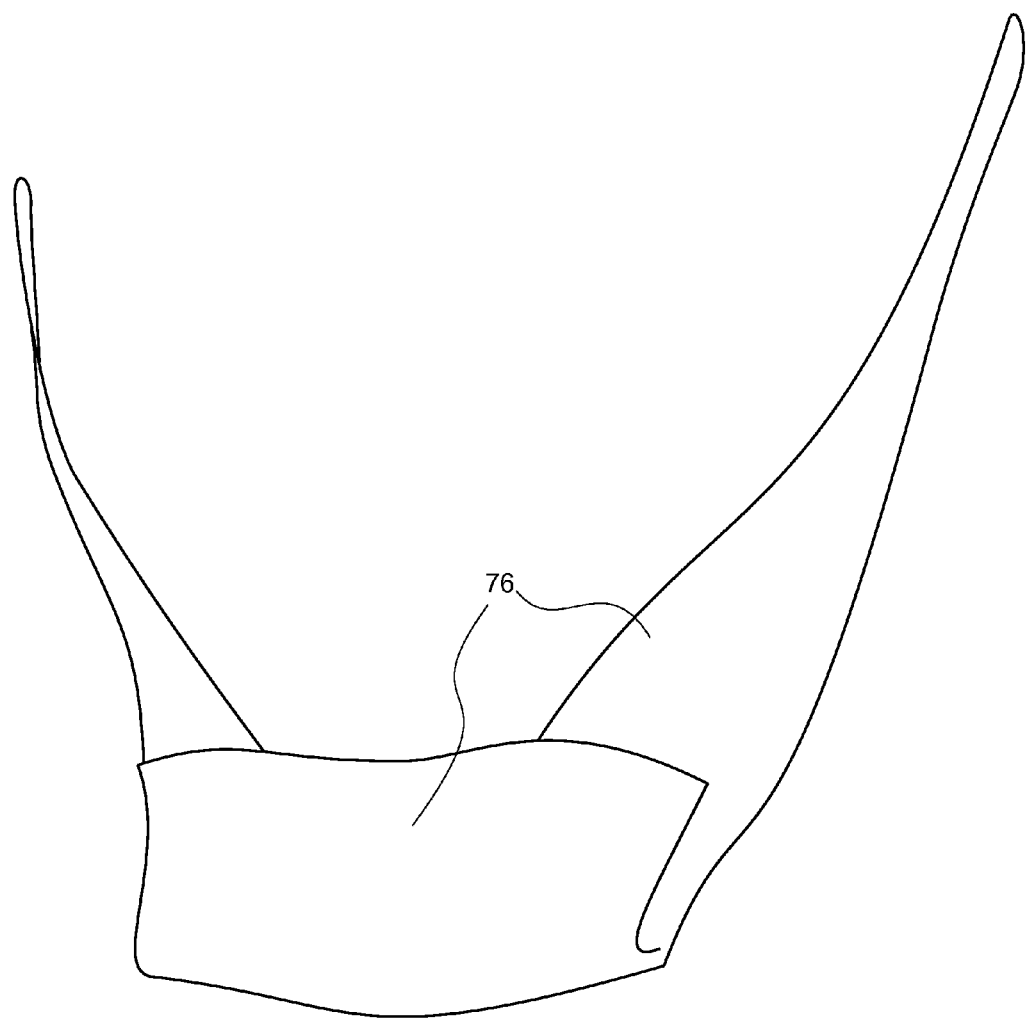
FIG. 17 shows a front view of a chin strap to be added as an accessory to hybrid sleep mask

The textile component 62 is comprised of a lower posterior component 69, FIGS. 14, 15 which become the origin of lower strap 72 that goes anteriorly; an upper posterior component 70, FIGS. 14, 15, into which distal end of upper strap 71 pulls through and back onto itself; anterior component 58, FIG. 14, with a loop or tunnel 79 through which strap 72 pulls through anteriorly and then back onto itself; upper strap 71 also originates from component 58; and mounds 68 that are located on the posterior sides of the foot pads. The mound(s) 68 are formed in part by the stretchable or non-stretchable material 62 of component 58 but a gel-like material can be added that can be slightly tacky, such as polyurethane or a thermoplastic elastomer to cover the textile mound which in turn will contact the user's face. This gel like mound (not shown) can have Velcro hook backing and can be attached to the posterior side of the pocket 77 by hook Velcro with gel located on the medial side for contact with user's face. Increased thicknesses of the gel mound with a Velcro backing can be used to elevate the bridge away from a user's nose and thereby separate the bridge from contacting a user's nose. The hybrid sleep mask 60 can be adjusted, and/or relocated so that the mound 68 is located at the same or different location(s) in relation to user's nose and/or face and/or head to improve nasal patency and/or patient comfort. Adjustment of straps and configuration of the hybrid sleep mask allows a user to move the mound 68 to different location(s) on the user's face to obtain desired comfort and improved nasal passage opening.

In FIG. 15, component 70 can be reversibly or irreversibly attached by Velcro means onto the superior border of section 69 that fits around the back of user's head to permit contact on the more superior-posterior region of the user's head and allows adjustment of vertical length to fit the configuration (size and shape) of the superior-posterior regions of the user's head. Straps 71 extend superiorly and/or posteriorly above the user's ears and then pull through openings in top of section 70 and back onto itself with Velcro attaching means. Pulling upper straps 71 through openings in section 70 creates an adjusting means for length tightening or loosening the hybrid sleep mask 60 for comfort fit. Attachment of lower straps 72 to component 69 allow user to pull lower straps 72 anteriorly through tunnel 79 on component 58 and attach back onto itself for tightening with Velcro means. Tightening lower 72 straps through and/or tightening upper straps 71 will allow better fitment to different facial and head configurations and permit the device to cause lateral and other vectored forces to be imposed onto housing foot pads 66, which in turn transmit forces onto mounds 68 to open the user's nasal valves as well as maintain the hybrid sleep mask in place. The rigid or semi-rigid housing 61 with a bridge 63 provides means for maintaining adjusted forces for nasal dilation for either or both sides of user's nose.

In summary, the hybrid sleep mask 60 when worn is first adjusted for optimal vertical extension by attaching components 69 and 70 using Velcro or other attaching means, such as snaps, etc. Then upper 71 and lower straps 72 are pulled into optimal positions for user comfort and optimal nasal passage dilation. The mounds 68 contact both sides of the user's face such as the cheeks and/or around the user's nose. When the hybrid sleep mask is worn with tightening means provided by straps 71 and 71, various vectored forces, including the lateral vector of the Cottle effect, are applied onto the mounds 68 and thereby onto the underlying skin and fascia attachments to the nasal valves and/or vestibules, which in turn open the nasal valves and/or vestibules. The bridge should ideally not compress the user's nose if properly adjusted.

In an aspect, additional mounds may be added to position the mask on optimal locations to open the nasal passages when worn on a user's face. This embodiment made of soft stretchable or other soft non-stretchable materials may be used for sleep to minimize nasal airway collapse when a user lies in a supine or side position. An accessory chin support 76, FIGS. 13 and 17, can be reversibly or irreversibly added to the hybrid sleep mask 60 when worn on individuals whose mouth opens while in deep sleep patterns. To minimize dry mouth and/or oral-pharyngeal vibrations, the straps of chin support 76 can easily attach to straps 71 by Velcro or other attaching means.

In an aspect, hybrid sleep and/or exercise mask 80 with a nasal dilator device can be in the form of another embodiment. FIGS. 20-24 show a hybrid nasal dilating device for these applications. It is comprised of a rigid or semi rigid housing 81 with a bridge 82 that is located over the user's nose; extensions 88 that position around the user's nose that have foot pads 84; a head retainer strap tightening means 83; mound 87 attached to foot pads 84; handle slots 85, 86 for attaching head retainer strap 83 to housing 81 as seen in FIG. 22. FIG. 21 shows an embodiment of a rigid or semi rigid housing 81 that can bridge the nose without causing compressive pressure directly onto the nose of a user. The mound 87 is cylindrical in shape and provides separation of the foot pads 84 from the user's face. The angle of the bridge 82 (not seen in this perspective) is angled forward anteriorly in relation to extensions 88, so when the device 81 is worn, the bridge will move anteriorly away from contacting the user's nose. Without being limited according to the nasal dilator devices of the invention, the housing may be comprised of a variety of rigid and/or semi-rigid materials, in addition to the preferred plastic or plastic-like material, including those having different tensile strengths.

The ballooning expanse and shape of the bridge 82 can be any geometry that minimizes contact and compression onto the user's nose when the housing is applied to the face of a user. The extensions 88 on both sides of the housing 81 include foot pads 84 which can be angled at any angle such as ninety degrees from the extensions, although the angle can be more acute or more oblique, including for example having angles from the extensions at approximately one hundred and eighty degrees or less or more, depending on preference for user comfort and device functionality to open nasal valves.

Figure 20:
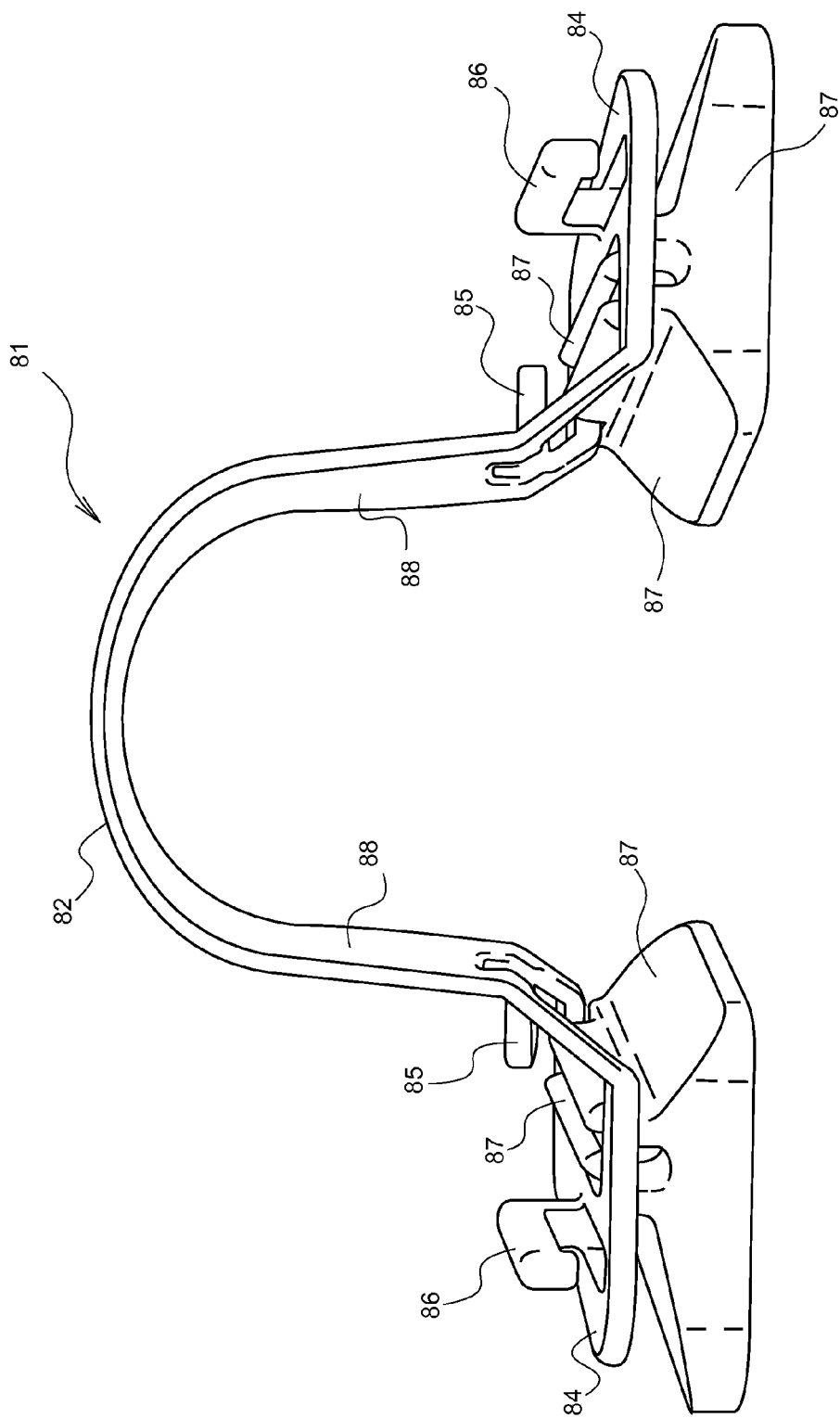
FIGS. 20 and 21 show rigid and/or semi-rigid housing embodiments as part of a nasal dilating device for an exercise mask application.
Figure 21:
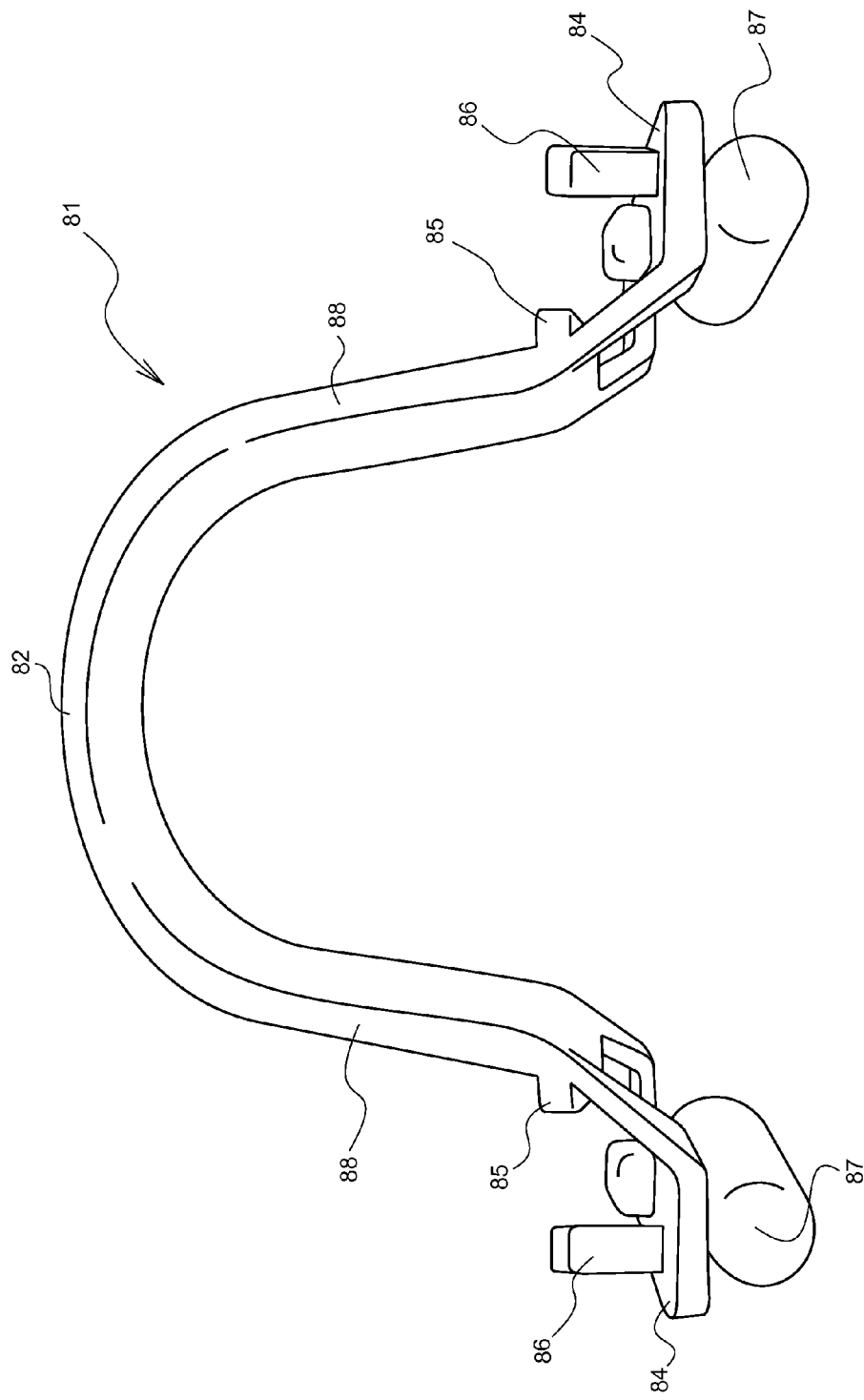
Figure 22:
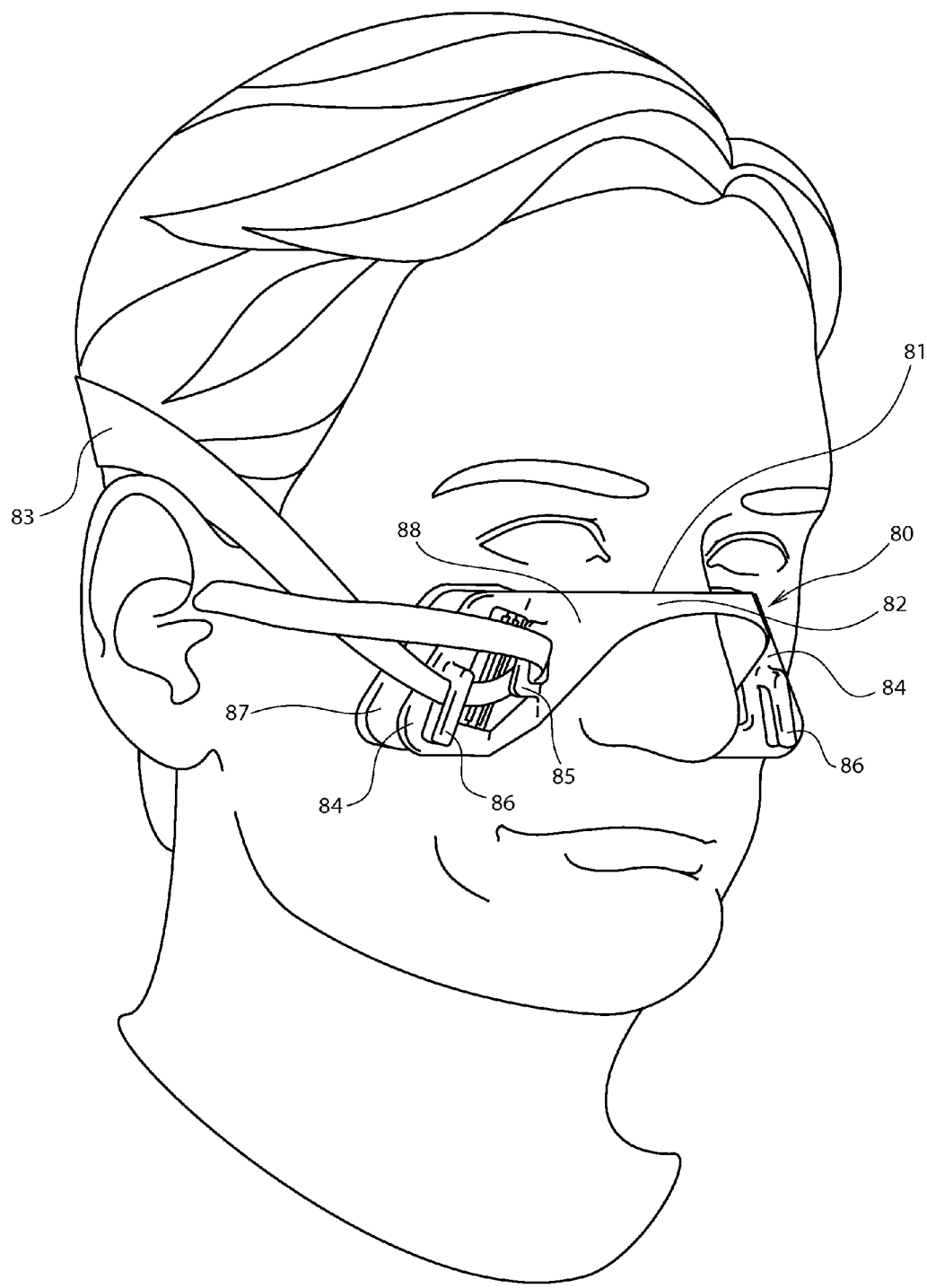
FIG. 22 shows a user wearing an exercise mask with a semi-rigid or rigid housing comprising a bridge located over the nose, and having attachment straps, according to an embodiment of a nasal dilator device for this application.

In an aspect, FIGS. 20, 21, mounds 87 can snap or otherwise affix themselves into the foot pads 84. According to embodiments of the invention, the mounds 87 located on the foot pads 84 are configured in different sizes, materials and/or shapes for user comfort and be of a variable height to move the bridge 82 of the housing 81 anteriorly and away from contacting the user's nose when the head retainer straps 83 pull laterally to open and maintain patency of the nasal valves per the Cottle effect. The mounds 87 can be configured to flex when the housing 81 is worn with head retainer straps 83. Moreover, according to the methods of use of the nasal dilator devices, the flexing capability of the mounds 87 add moments of force to the underlying locations on the user's face when the head retainer straps are pulled laterally.

FIG. 22 shows a user wearing a nasal dilator device for these applications comprised of head retainer straps 83 that fit snugly around the head and/or ears of a user. In a non-limited aspect of the invention, such head retainer straps 83 can be made from silicone, bungee cords made of rubber or non-latex rubber such as synthetic neoprene, or other elastic materials such as thermoplastics and stretchable textiles. The straps 83 are designed to be looped and/or otherwise attached through handles slots 85, 86 located on the extensions 88 or the foot pads 84. The head retainer straps 83 can be wrapped around the head of the user above the ears and/or below the ears or both, and the free ends of the straps can return towards the housing and slip into a second set of handle slots 85, 86 as seen in FIG. 22.

The posterior surface of the mounds that contact the user's skin can have grooves that function to drain away sweat that may accumulate under the mounds during physical exercise. These and other modifications of the shape and size of the mounds are included within the scope of the invention disclosed herein. Additionally, mounds can be any functional shape such as dome-convex shape with the apex approximating the contact point on the user's face or a cylindrical shape 87 shown in FIG. 22. It is noteworthy that mound 87 in FIGS. 20, 21 can be located below the horizontal plane of foot pad 84. This allows the mound 87 to be positioned inferior to the foot pad 84 and permits the mound to touch user's face with less likelihood of foot pad 84 doing the same.

Additional mounds can also be placed on the underside of the bridge 82 of the housing 81 for several indications. A mound added to underside of bridge 82 can hold tip of a user's nose if it is prolapsed and impairing nasal patency. The skin overlying the nose can be pulled taut superiorly and slightly posteriorly under the mound positioned on the underside of bridge 82 of housing. The tip of the user's nose is thereby pulled away from the upper lip to improve nasal patency.

Figure 23:
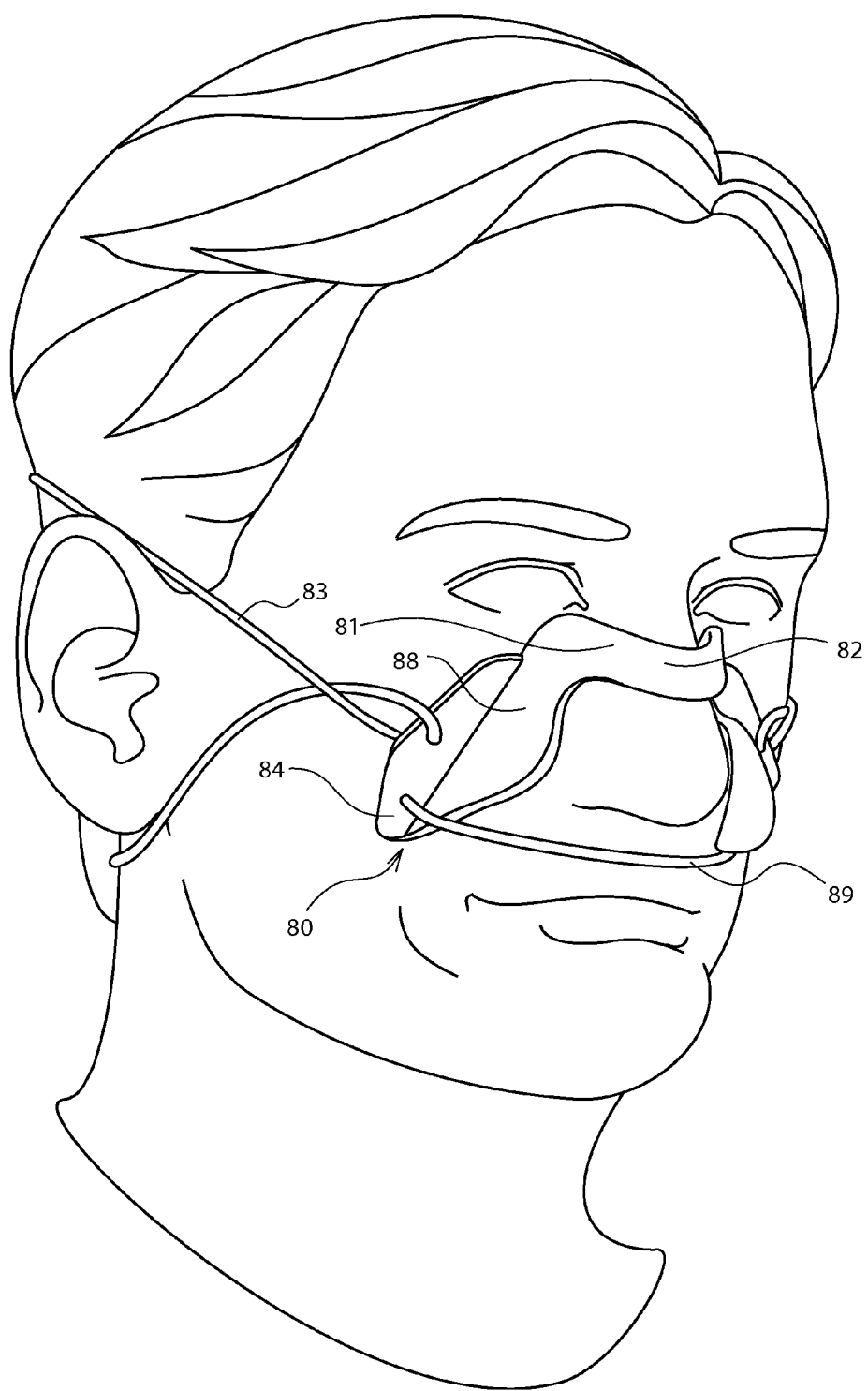
FIG. 23 shows a user wearing an exercise mask with a semi-rigid or rigid housing comprising a bridge located over and below the nose, and having attachment straps, according to an embodiment of a nasal dilator device for this application.
Figure 24:
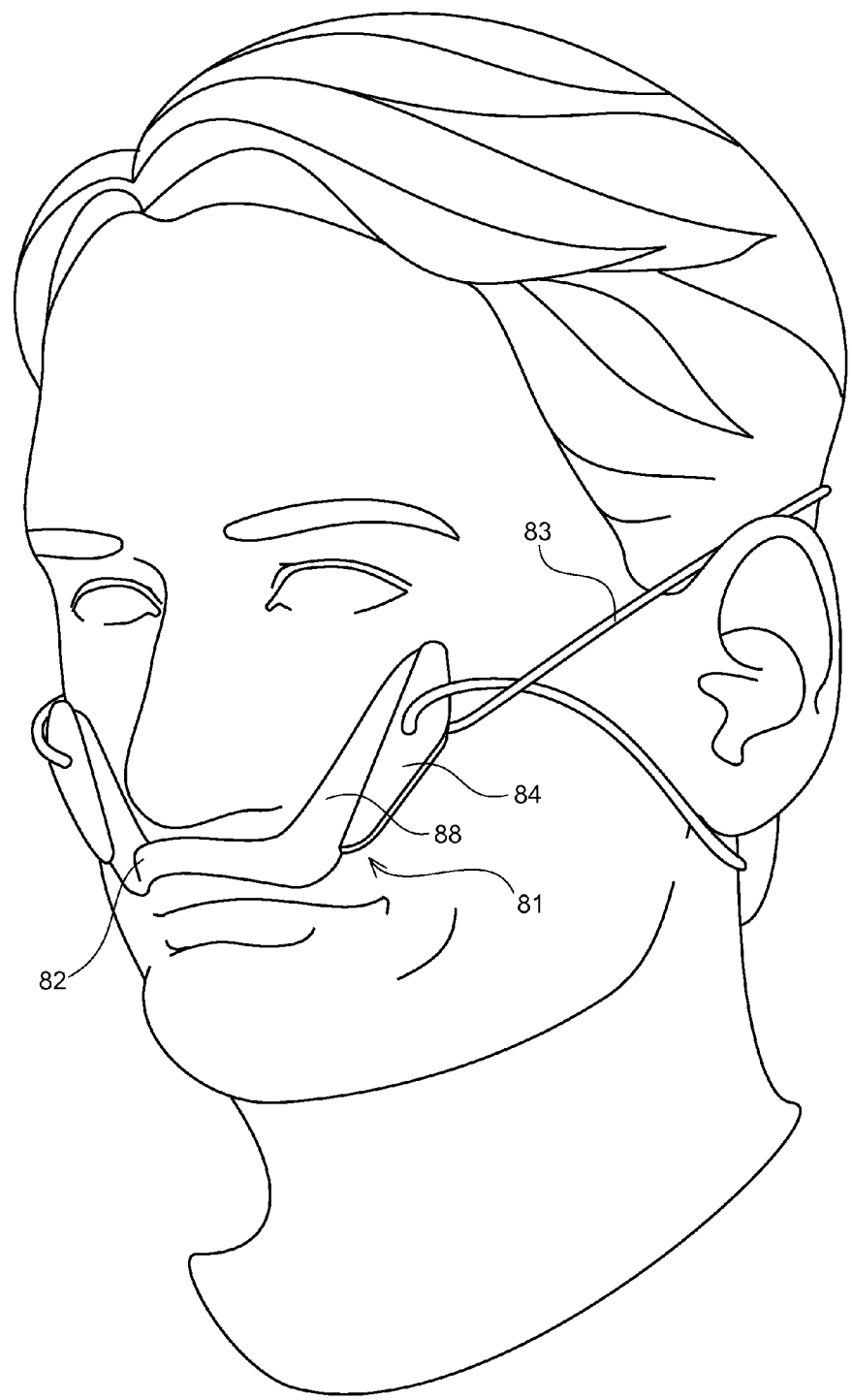
FIG. 24 shows a user wearing an exercise mask with a semi-rigid or rigid housing comprising a bridge located below the nose, and having attachment straps, according to an embodiment of a nasal dilator device for this application.

As disclosed herein, the housing 81 takes advantage of moments of forces provided by the increased height of mounds 87, such that when tightening means of head retainer straps 83 are pulled laterally, there are increased forces (s) applied directly onto the mounds and underlying skin with anatomical attachments to the nasal valves and/or vestibules, thereby opening and improving patency of the nasal valves and/or vestibules. Other mounds can also be added to the housing in combination with the nasal-facial junction located mounds. The rigid or semi-rigid housing 81 with a bridge 82 provides means for maintaining adjusted forces for nasal dilation for either or both sides of user's nose The rigid and/or semi-rigid housing 81 can include a second lower bridge 89, as shown in FIG. 23. A lower bridge 89 may be added to the housing 81 to hold extensions 88 and foot pads 84 with mounds (not seen) from spreading too far laterally when user wears housing 81 with strap 83 and thereby prevents the bridge 82 from contacting and/or compressing user's nose. In yet another embodiment of the rigid and/or semi-rigid housing 81, as shown in FIG. 24, the housing 81 can be situated so that the bridge 82 overlies the region below the user's nose and above the upper lip. Pulling laterally on the head retainer strap 83 causes extensions 88 and foot pads 84 (with mounds 87, not shown) to move laterally, and thereby open the nasal valves as previously described. The bridge 82 could also be positioned above the user's nose around the lower forehead (not shown) and have extensions 88 and foot pads 84 with attached mounds 87 positioned around the user's nose at optimal locations to open the nasal valves.

As described herein, the components of these hybrid mask devices described herein for sleep and/or exercise with inclusion of a mound 68, 87 have all Essential Elements according to the invention of a nasal dilator device, including: (1) a rigid or semi-rigid housing 61, 81 with a bridge 63, 82 respectively; (2) the bridges 63, 82 as part of the housing located at any single or combination of locations over, above or below the user's nose to distribute nasal dilating forces to either or both sides of the user's nose and/or face; (3) mounds 68, 87; (4) a holding means for mound 68 created by pocket 77 that contains foot pad 66 onto which mound is formed on posterior side of pocket, with or without addition of a soft mound that has direct contact with user's face and holding means of mound 87 onto foot pads 84; (5) a means for attachment of tightening means by attaching head retainer straps 71,72 to housing 61 and attachment of tightening means of head retainer straps 83 to housing 81; (6) varying tightening means of head retainer straps 71, 72 onto mound(s) 68 and varying tightening means by head retainer straps 83 onto mound 87, thereby onto underlying skin and anatomical attachments to enhance nasal valve and/or vestibule opening; (7) ability to adjust, and/or relocate mound(s) 68, 87 to same or different location(s) in relation to user's nose and/or face and/or head as needed to improve nasal patency and/or patient comfort; and (8) reusability.

Nasal Dilating Devices for CPAP Mask Application

Figure 19:
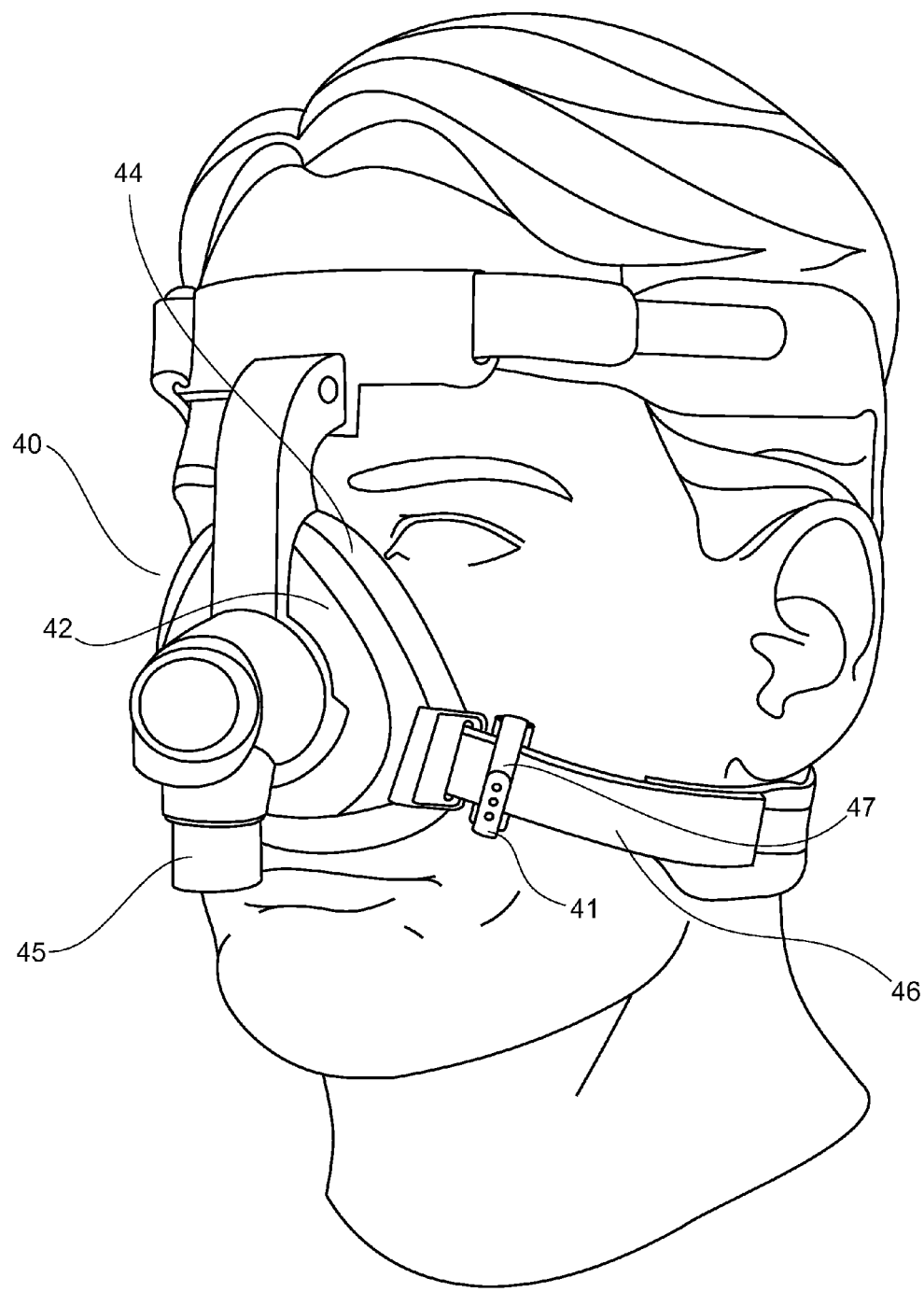
FIG. 19 shows cylindrical mounds attached to head retainer straps of a nasal CPAP mask on a user, according to an embodiment of a nasal dilator device for this application.

In another application, mounds 41 can be added onto a nasal CPAP 40, FIG. 19, or full face CPAP mask (not shown), both comprising a rigid or semi-rigid housing 42, also referred to as a shell, comprising a bridge (not numbered as it is part of the housing 42) that covers the user's nose, mouth or any combination thereof; head retainer straps 46 connected to the housing 42; cushion liner 44 that interfaces the housing 42 of the mask and user's face and surrounds a user's nose or around the combination of a user's nose and mouth; and a hose attachment 45 to connect to a CPAP compressor. A nasal CPAP mask shown in FIG. 19 covers completely above, over and occasionally below a user's nose, and a full face CPAP mask covers above, over and below a user's nose and includes coverage over the user's mouth.

There are variants of nasal CPAP devices which have prongs or pillows (not shown), that are inserted into the nasal cavities, and do not surround above or over the user's nose. However they have a semi-rigid or rigid housing that positions these atypical CPAP nasal mask(s) below the user's nose to allow means for distribution of tightening forces to both sides of the user's nose and other facial features. Hence as will be understood, they have all the Essential Elements needed for the nasal dilating device to function.

Figure 18:
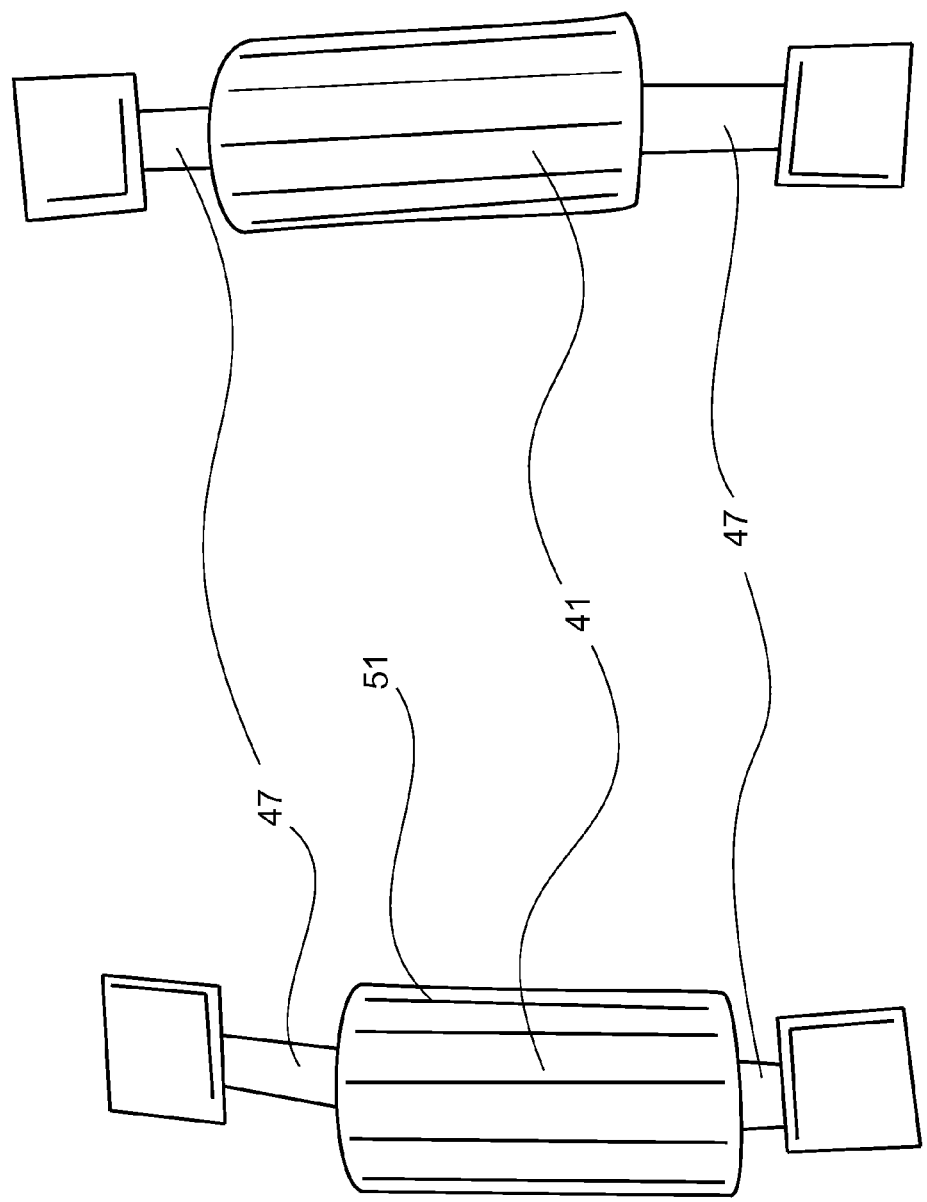
FIG. 18 shows compressible cylindrical mound with straps to attach reversibly or irreversibly around a head retainer strap of a CPAP mask, according to an embodiment of a nasal dilator device for this application.

In an aspect as shown in FIGS. 18, 19, cylindrical soft material compressible mounds 41 can be added as an accessory onto the head retainer straps 46 of either type of CPAP mask, as seen in FIG. 19 for the nasal type mask. FIG. 18 shows the mounds 41 in further detail detached from the CPAP mask. The mounds 41 can have intrinsic holding means with ridges 51 and/or grooves to help maintain their contact on the user's skin and also to allow any nighttime perspiration to dissipate away from the mounds. In one embodiment, the mound 41 has straps 47 with two ends with means to attach around the CPAP head retainer straps 46. Example attaching means of mound(s) 41 to the head retainer straps 46 can be Velcro hook and loop, or connecting means comprising snaps or protrusions on strap ends into complementary snaps or holes in the other strap ends. The mounds 41 can also have other means for attachment such as slots in the mounds 41 to slide into the head retainer straps 47. The mounds approximate the user's face and are additionally held in place by the tightening means of the head retainer straps 46.

Once the CPAP mask is placed on the user's head with attached head retainer straps 46, then the mound 41 can be placed under head retainer straps 46 to contact user's face and moved laterally or medially to obtain the optimal skin pull to open the user's nasal valves and/or vestibules. Tightening the head retainer strap 46 onto mound 41 can cause the mound 41 to rotate to create more lateralizing and other functional vectored pull on the underlying skin and anatomical attachments to the nose, which enhance opening the nasal valves and/or nasal vestibules. The rotation may be clockwise or counter clockwise to accomplish opening of the nasal valves and/or vestibules. It is understood that the mounds 41 can be reversibly and/or irreversibly integrated in the manufacture of the nasal and/or full face CPAP masks, such as in the head retainer straps 46 or be an accessory as described in FIGS. 18 and 19 to add onto the head retainer straps 46 of the masks. It is also possible to integrate mounds 41 reversibly or irreversibly on the outside or inside of the mask. The shape of the mound 41 can be configured to any shape(s) and/or constructed of any material to accomplish the function of opening the nasal valves according to the embodiments of the invention. The rigid or semi-rigid housing 42 with a bridge provides means for maintaining adjusted forces for nasal dilation for either or both sides of user's nose.

In addition mounds 41 placed at strategic locations along CPAP head retainer straps 46 for full face CPAP masks and nasal CPAP masks 40, can have other beneficial effects besides nasal passage opening. For one, stretching forces created by forces applied to the mounds by tightening of the head retainer straps 46 enhance approximation and better seal of the CPAP cushion liner 44 onto the user's face and thereby reduce air leaks between the interface of the CPAP mask and user's skin. This is especially helpful to improve approximation and seal of the lower end of the cushion liner of a full face CPAP to the anterior mandible of a user, and as such minimize opening of user's mouth which can cause movement of the lower end of cushion liner 44 up into the user's mouth and thereby interrupt the pressure seal for CPAP. In addition mounds 41 placed over the rami of the mandible and the maxillary bones serve to hold them together and thereby cause some restriction to opening the user's mouth, especially if placed closer to the temporal-mandibular joint. Location over the user's cheeks can also control puffing-out of cheeks from buildup of air pressure within the respiratory tract that can occur abruptly while asleep and cause awakening of the user.

Mounds 41 in summary: (1) serve to open nasal valves in combination with the tightening means of the CPAP head retainer straps, which in turn can reduce the tendency for CPAP mask users to switch to mouth breathing; (2) control or minimize puffing-out of cheeks and (3) reduce air leaks from the CPAP mask interface with the user's face by increasing moments of forces that tighten the cushions of the masks against the user's face.

In addition a stretchable or non-stretchable chin strap (not shown) can be positioned under and/or around the user's chin. The chin strap can have end-straps with Velcro attaching means that can loop around the CPAP head retainer straps 46 and then attach back onto the underside of the chin strap with complementary Velcro. The chin strap can be positioned between the mounds 41 to maintain their positioning if needed, and it can serve to keep the jaw of user from relaxing and opening which can cause movement of the lower end of cushion liner up into the user's mouth and thereby interrupt the pressure seal for CPAP.

The components of a CPAP mask application including the addition of mound(s) 41 have all the Essential Elements according to the invention for functioning of a nasal dilating device, including: (1) A rigid or semi-rigid housing 42 with a bridge providing means for maintaining adjusted forces for nasal dilation for either or both sides of user's nose; (2) the bridge as part of the housing 42 located above, over and below the nose for a nasal CPAP mask and for a full face CPAP mask with the bridge as part of the housing 42 is located over, above, below the nose and over the mouth, both distributing nasal dilating forces to both sides of a user's nose and/or face; (3) mound(s) 41; (4) holding means for mounds 41 under CPAP head retainer straps 46 and/or with mound straps 47 around CPAP head retainer straps 46 to maintain mound 41 positioning; (5) means for attaching tightening means comprised of head retainer straps 46 to housing 42; (6) tightening means of head retainer straps 46 with capability of varying forces onto mound(s) 41 and thereby onto the underlying skin and anatomical attachments to open nasal valves and/or vestibules; (7) ability to adjust, and/or relocate mound(s) 41 to same or different location(s) in relation to user's nose and/or face and/or head as needed to improve nasal patency and/or patient comfort; and (8) reusability.

Summation of Applications with Nasal Dilator Device

In each of the various nasal dilator devices for each named application, the housings and/or stretchable/or non-stretchable components and mounds may be made of various materials. For example, in an embodiment the housings may be made of various materials, preferably plastic materials and one may envision various aesthetic modifications which may be employed, including use of translucent materials, colors, patterns, etc. Similarly, the stretchable or non-stretchable components of embodiments of the invention may further be provided in various colors, patterns, etc. for purposes of aesthetics. The mounds can be comprised of softer materials such as elastomeric composition, polyurethane or other similar plastics and textiles.

In each of the various nasal dilator devices for each named application, the holding means may be achieved or provided through multiple mechanisms for maintaining or holding in place the mound(s) of the nasal dilator devices in order to maintain their positioning. In the various embodiments the holding means provides friction or pressure to maintain positioning of the mound(s). Exemplary holding means include inward pressure of a head retainer strap onto mound(s), the interface between mound(s) and a helmet or sides of the user's head, projections on mound(s) for providing contacting, friction, interlocking or the like with a retainer strap, helmet or the like.

An advantage of this invention is now apparent as it provides the necessary means to accomplish its proposed goals, namely opening nasal external and/or internal valves and/or vestibules and controlling nasal tip prolapse. It utilizes lateral and/or other vectored forces that can be maintained during sleep with a hybrid mask or with a CPAP mask, for exercise with a hybrid mask, for goggles alone or with a helmet, and for swim goggles alone or with a swim cap. The nasal dilating devices with applications can be adjusted for comfort and for optimization of nasal valve patency. They are customizable, inexpensive to reproduce and manufacture, washable, adjustable and reusable.

The various applications of the nasal dilating device according to the invention are suitable for use and wear during periods of activity and during sleep to improve and/or maintain nasal patency of the nasal valves and thereby enhance nasal airflow and breathing. Periods of use include for example, wearing the devices during exercise to optimize nasal breathing, such as for aerobic activity involving runners, dirt motor bikers, military users wearing tactical goggles and helmets, skiers, snow-boarders, swimmers and for snowmobile activity. Beneficially, the various nasal dilating device applications provide comfort for the user both during sleep and/or during physical activities Beneficially, the methods of use open the user's nasal valves, and can further be adjusted, removed, reused and/or retained on the user without easily falling off during sleep or during physical activity and exercise. As a still further benefit, the methods of use may further employ customizing with alterations of dimensions, shape, and/or material composition, so that users with different facial and head shapes and/or nasal dimensions can wear the nasal dilating device applications and still accomplish the same function to open the nasal valves.

In another aspect of the methods of use, the nasal dilator devices can be integrated into applications using goggles, a helmet, CPAP mask, and swim goggles alone or with swim caps, or it can be added as an accessory with these applications.

In a further aspect of the uses according to the invention, by improving nasal breathing, nasal dilating device applications aid in warming and humidifying cool air as it is breathed through the nose into the lungs, reducing dry mouth, filtering air through the nose, reducing tendency for dental caries, and cold induced and exercise induced bronchospasm.

What is claimed is:

1. A reusable, re-adjustable, and re-locatable nasal dilator device comprising:
    a rigid or semi-rigid housing with an integrated bridge connected thereto said housing located at any single or combination of locations over, above and below a user's nose;
    mounds positioned by a means of holding on both sides of the user's face at a location extending lateral to the user's nose to apply lateralizing forces to pull the user's underlying skin to open nasal passages, wherein the means of holding for said mounds support said mounds in place to apply the lateralizing forces;
    varying tightening means attached to said housing providing the lateralizing forces onto said mounds, wherein said tightening means is a strap and is adjustable to provide the lateralizing forces onto said mounds thereby transmitting the lateralizing forces onto the underlying skin of said user to open the user's nasal passages to improve nasal patency of said user, and
    wherein said housing and said bridge provide means for said forces to maintain said nasal patency to either or both sides of said user's nose.

2. The device of claim 1 further comprising one or more of the following components: (A) goggles having a cushion liner and a head retainer strap or goggles having a cushion liner and a head retainer strap in combination with a helmet; (B) swim goggles with a cushion liner and head retainer straps and optionally with a swim cap; (C) a hybrid sleep mask with head retainer straps; (D) an exercise mask with head retainer straps; and (E) CPAP mask with a cushion liner and head retainer strap(s).

3. The device of claim 2 wherein said housing for said goggles and swim goggles include a translucent barrier over eyes of said user.

4. The device of claim 2 comprising said goggles wherein said head retainer strap attached to said housing provides said holding means for said mounds and varying tightening means onto said mounds when said mounds are positioned and held between said goggles with said head retainer strap and said helmet.

5. The device of claim 4 wherein said holding means and said tightening means for said goggles lateralizes positioning of said cushion liner on face of said user to reduce focalized pressure around user's nose with said goggles, and provides increased barrier against entry of detrimental environmental influences between said cushion liner and user's face for said goggles.

6. The device of claim 2 comprising said goggle component (A) wherein said mounds can be increased in apical height and slope by attachment of add-on plates or add-on segments to said mounds.

7. The device of claim 2 comprising said goggle component (A) with said cushion liner and a head retainer strap used in combination with said helmet, wherein said mound is an accessory with means for attachment to said goggle head retainer strap and is comprised of a compressible material.

8. The device of claim 7 comprising said goggles component (A) wherein said mounds provide height to stretch said head retainer strap and thereby create forces onto said cushion liner to open nasal airways of a user.

9. The device of claim 7 wherein said mounds are an insert added onto said helmet with an attaching means.

10. The device of claim 9 wherein said attaching means is provided by channel(s) comprising a rail and lip integrated into the manufacture of both sides of a helmet.

* * * * *